US012599331B2

(12) United States Patent
Shaked et al.

(10) Patent No.: US 12,599,331 B2
(45) **Date of Patent: \*Apr. 14, 2026**

(54) HYPERSPECTRAL IMAGE-GUIDED OCULAR IMAGER FOR ALZHEIMER'S DISEASE PATHOLOGIES

(71) Applicant: RETISPEC INC., Toronto (CA)

(72) Inventors: Eliav Shaked, Toronto (CA); Grzegorz Dmochowski, Toronto (CA)

(73) Assignee: RETISPEC INC., Toronto (CA)

( * ) Notice: Subject to any disclaimer, the term of this patent is extended or adjusted under 35 U.S.C. 154(b) by 121 days.

This patent is subject to a terminal disclaimer.

(21) Appl. No.: 18/538,524

(22) Filed: Dec. 13, 2023

(65) Prior Publication Data

US 2024/0341668 A1      Oct. 17, 2024

Related U.S. Application Data

(63) Continuation of application No. 16/766,880, filed as application No. PCT/CA2018/051504 on Nov. 27, 2018, now Pat. No. 11,896,382.

(Continued)

(51) Int. Cl.
*A61B 5/00* (2006.01)
*A61B 3/00* (2006.01)
(Continued)

(52) U.S. Cl.
CPC .......... *A61B 5/4088* (2013.01); *A61B 3/0025* (2013.01); *A61B 3/1225* (2013.01);
(Continued)

(58) Field of Classification Search
CPC ... A61B 5/4088; A61B 3/0025; A61B 3/1225; A61B 3/14; A61B 5/0075; A61B 5/7264;
(Continued)

(56) References Cited

U.S. PATENT DOCUMENTS 6,419,361 B2    7/2002   Cabib et al.
6,849,249 B2    2/2005   Goldstein et al.
(Continued)

FOREIGN PATENT DOCUMENTS

CA          3039858 A1    4/2018
WO      2010019515 A2    2/2010
(Continued)

OTHER PUBLICATIONS

Michael et al., "Hyperspectral Raman Imaging of Neuritic Plaques and Neurofibrillary Tangles in Brain Tissue from Alzheimer's Disease Patients," Scientific Reports, vol. 7:156003, pp. 10; Nov. 15, 2017.
(Continued)

*Primary Examiner* — Michael J Carey
*Assistant Examiner* — Zainab Mohammed Aldarraji
(74) *Attorney, Agent, or Firm* — Greenberg Traurig, LLP; Roman Fayerberg; Richard Brooks

(57)      ABSTRACT

A non-invasive device for detecting Alzheimer's Disease-associated pathologies, comprising a fundus camera comprising a spectral reflectance imaging unit that includes a broadband light source and a light sensor and a lens assembly to focus light from the broadband light source onto a fundus of an eye, and one or more processors to detect reflected and/or backscattered light from the eye, illuminated by the broadband light source, using the light sensor for determining spectral reflectance information, generate a plurality of spectral reflectance maps comprising counts of reflected and/or backscattered light at a different wavelength or a different range of wavelengths, assign a weight to each of the spectral reflectance maps, and determine one or more regions of interest from the weighted spectral reflectance maps as being a potential Alzheimer's Disease-associated
(Continued)

pathology based on a detection of one or more biomarkers indicative of Tauopathy.

27 Claims, 18 Drawing Sheets

Related U.S. Application Data

(60) Provisional application No. 62/590,836, filed on Nov. 27, 2017.

(51) Int. Cl.

| | |
|---|---|
| *A61B 3/12* | (2006.01) |
| *A61B 3/14* | (2006.01) |
| *G01N 1/28* | (2006.01) |
| *G01N 1/30* | (2006.01) |
| *G01N 21/55* | (2014.01) |
| *G01N 21/65* | (2006.01) |
| *G01N 33/68* | (2006.01) |

(52) U.S. Cl.
CPC .............. *A61B 3/14* (2013.01); *A61B 5/0075* (2013.01); *A61B 5/7264* (2013.01); *G01N 1/286* (2013.01); *G01N 1/30* (2013.01); *G01N 21/55* (2013.01); *G01N 21/65* (2013.01); *G01N 33/6896* (2013.01); *G01N 2001/2873* (2013.01); *G01N 2333/4709* (2013.01); *G01N 2800/2821* (2013.01)

(58) Field of Classification Search
CPC ..... A61B 2576/02; A61B 5/7267; A61B 3/12; G01N 1/286; G01N 1/30; G01N 21/55; G01N 21/65; G01N 33/6896; G01N 2001/2873; G01N 2333/4709; G01N 2800/2821; G16H 30/40; G16H 50/70
See application file for complete search history.

(56) References Cited

U.S. PATENT DOCUMENTS

| | | | |
|---|---|---|---|
| 6,988,995 | B2 | 1/2006 | Zhou et al. |
| 7,107,092 | B2 | 9/2006 | Goldstein et al. |
| 7,297,326 | B2 | 11/2007 | Goldstein et al. |
| 7,653,428 | B2 | 1/2010 | Goldstein et al. |
| 8,787,638 | B2 | 7/2014 | Zee et al. |
| 8,814,362 | B2 | 8/2014 | Verdooner |
| 8,955,969 | B2 | 2/2015 | Hartung et al. |
| 9,149,184 | B2 | 10/2015 | Campbell |
| 9,220,403 | B2 | 12/2015 | Hartung et al. |
| 9,320,436 | B2 | 4/2016 | Russmann et al. |
| 9,451,909 | B2 | 9/2016 | Hartung et al. |
| 9,521,975 | B2 | 12/2016 | Verdooner et al. |
| 9,524,304 | B2 | 12/2016 | Jayasundera et al. |
| 9,566,000 | B2 | 2/2017 | Verdooner et al. |
| 9,585,558 | B2 | 3/2017 | Vince et al. |
| 9,730,580 | B2 | 8/2017 | Verdooner |
| 9,808,155 | B2 | 11/2017 | Verdooner |
| 9,839,699 | B2 | 12/2017 | Koronyo et al. |
| 9,854,963 | B2 | 1/2018 | Verdooner |
| 10,039,487 | B2 | 8/2018 | Verdooner et al. |
| 10,098,540 | B2 | 10/2018 | Vince et al. |
| 10,866,242 | B2 | 12/2020 | Farokhzad et al. |
| 10,964,036 | B2 | 3/2021 | Sylvestre et al. |
| 11,769,264 | B2 | 9/2023 | Sylvestre et al. |
| 11,896,382 | B2 | 2/2024 | Shaked et al. |
| 2005/0095653 | A1 | 5/2005 | Goldstein et al. |
| 2010/0105098 | A1 | 4/2010 | Frederiske et al. |
| 2011/0080577 | A1 | 4/2011 | Nelson et al. |
| 2011/0129133 | A1 | 6/2011 | Ramos et al. |
| 2011/0129134 | A1 | 6/2011 | Ramos et al. |
| 2012/0101371 | A1 | 4/2012 | Verdooner |
| 2014/0350379 | A1 | 11/2014 | Verdooner |
| 2016/0278677 | A1 | 9/2016 | Kerbage et al. |
| 2019/0022255 | A1 | 1/2019 | Koronyo et al. |
| 2019/0150733 | A1 | 5/2019 | Vince et al. |
| 2022/0157470 | A1 | 5/2022 | Sylvestre et al. |
| 2023/0394689 | A1 | 12/2023 | Sylvestre et al. |

FOREIGN PATENT DOCUMENTS

| | | |
|---|---|---|
| WO | 2013086516 A1 | 6/2013 |
| WO | 2016041062 A1 | 3/2016 |
| WO | 2016157156 A1 | 10/2016 |
| WO | 2020188471 A1 | 9/2020 |

OTHER PUBLICATIONS

International Search Report in International Application No. PCT/CA2018/051504 mailed Mar. 12, 2019.
European Search Report; EP18881468.5; Date: Jun. 28, 2021.

1102 — Performing hyperspectral reflectance imaging on wide field of view

1104 — Determine ROI of potential AD pathologies

1106 — Performing Raman spectroscopy on ROI

1108 — Classify AD pathologies or AD conclusion

1110 — Output AD classification or AD conclusion

1112

1100

1200

Slice sample and place on slides in series — 1202

Stain every second slide in the series — 1204

Identify plaques on each stained slide using histology — 1206

Co-register slides having plaques with adjacent non-stained slide — 1208

Perform imaging modality on non-stained slide — 1210

Classify imaging information from imaging modality as plaque — 1212

HYPERSPECTRAL IMAGE-GUIDED OCULAR IMAGER FOR ALZHEIMER'S DISEASE PATHOLOGIES

CROSS-REFERENCE TO RELATED APPLICATIONS

This application is a continuation patent application of U.S. application Ser. No. 16/766,880, filed May 26, 2020, which is a national stage entry of PCT International Application No. PCT/CA2018/0581504, filed Nov. 27, 2018, which claims the benefit of and priority to U.S. Provisional Patent Application No. 62/590,836 filed Nov. 27, 2017, the entire contents of each of which are incorporated herein by reference.

TECHNICAL FIELD

Example embodiments relate generally to ocular light-based diagnostic detectors for detection, localization, and quantification of Alzheimer Disease related pathologies in the eye.

BACKGROUND

Alzheimer's disease (AD) is a fatal neurodegenerative disease. Confirmation of the disease is commonly performed post-mortem. Some existing conventional systems for diagnosis involve either highly invasive procedures, or are inaccessible imaging devices due to cost or complexity, or use harmful radioactive tracers.

Some conventional biomarker methods are used to identify AD-associated pathology and are considered ancillary measures which may aid clinicians in detecting AD at earlier stages and differentiating its symptoms from other forms of dementia. These techniques often assess Amyloid brain deposition or downstream neuronal injury and include, for example: cerebral spinal fluid (CSF) measurements for Amyloid Beta (Af3) and phosphorylated-Taus (components of neurofibrillary tangles, NFTs), positron emission tomography (PET) imaging for Amyloid Beta or fluorodeoxyglucose (FDG) uptake (hypometabolism in parietal and temporal lobes), and magnetic resonance imaging (MRI) for brain atrophy. However, many of these techniques are highly invasive, slow (e.g., require external lab verification), expensive, complex, inaccessible or beyond the training of many clinicians, and insufficient to identify the early or asymptomatic stages of AD.

It is an object to provide a non-invasive light-based detection system that is easily operable and accessible by clinicians for screening patient populations for early detection of AD-associated pathologies, diagnosis, and tracking of patient response to preventative or treatment interventions. It is an object to perform detection without exogenous fluorescing agents, dyes, or tracers.

It is an object for the system to detect specific characteristics of the chemical constituents of parts of the eye for more specific determination of AD-associated pathologies.

SUMMARY

Example embodiments relate to a non-invasive ocular light-based detection device for detecting AD-associated pathologies in the eye. The device can be used for optical detection of part of the fundus, such as the retina. The device is a light-based tool that provides an accessible and non-invasive procedure for identifying at-risk populations of AD, diagnosis, and tracking treatment and intervention efficacy. The device uses two imaging modalities wherein the first imaging modality guides the operation of the second imaging modality. Using the first imaging modality, the device detects light reflected and/or scattered off of the retina from a broadband light source, to determine a location and size of one or more regions of interest (ROI) that require further interrogation. Using the second imaging modality, the device detects light that is re-emitted through a Raman scattering process, which is initiated by incoming laser light onto each ROI; this enables the device to detect Raman spectroscopy information, to detect counts of a specific wavenumber shift or shifts that are characteristic of the chemical constituents of one or more AD-associated pathologies with high specificity.

The device is a non-invasive tool with sensitivity and specificity for detection of one or more AD-associated pathologies and can be used for pre-screening, diagnosis, and for tracking treatment and intervention efficacy. Conventional optical methods for non-invasive detection can suffer from lack of specificity and sensitivity, or may rely on exogenous fluorescing agents, dyes, or tracers.

The two imaging modalities are used in sequence for the determination of the presence of AD-associated pathologies indicative of AD. For the first imaging modality, a light source (for example a broadband lamp or monochromatic, patterned light) is used to acquire a wide field-of-view reflection-based image of the subject's retina, using hyperspectral imaging in an example embodiment. The first imaging modality allows for the detection of abnormal regions that may be protein oligomers or aggregates based on their physical properties and identifies a location and size of one or more ROI, which are then further interrogated by the second imaging modality using a second light source, such as a monochromatic laser. The monochromatic laser probes each ROI to see if there is effected a specific wavenumber shift or shifts that are characteristic of the chemical constituents of these AD-associated pathologies using Raman spectroscopy in an example embodiment. Raman spectroscopy is a highly specific method of detecting protein aggregates or other features that are characteristic of AD, or precursors of AD. In Raman spectroscopy, the targets of interest (for example, protein aggregates or other features) respond to the monochromatic laser by re-emitting (Raman scattering) light that is characteristic of the chemical constituents. This Raman scattered light is collected by the device and spectrum analyzed for the detection of chemical signatures of AD-associated pathologies.

The device does not rely upon exogenous fluorescing agents, dyes, or radioactive tracers. It is entirely non-invasive, exploiting two distinct imaging modalities, which work synergistically to yield high sensitivity as well as high specificity of detection of AD-associated pathologies, such as Tauopathy, soluble and/or insoluble Amyloid Beta species, Amyloid precursor protein (APP), as well as surrounding neuritic and glial cytopathology and vascular characteristics.

In some examples, the device uses a machine learning algorithm for operation of the device and for classification of optical information acquired from the subject's fundus, including the retina. The device allows for the rapid and non-invasive pre-screening of at-risk populations for AD disease, diagnosis, and tracking treatment and intervention efficacy (positive or negative responsiveness). Although many current non-invasive optical methods of AD detection in the retina rely on the use of exogenous fluorescing agents, the device uses endogenous optical contrast and Raman resonances in the eye for high-specificity detection of AD-associated pathologies, without the use of exogenous fluorescing agents.

In some examples, the machine learning algorithm is implemented by the device in two steps: first to identify the regions of interest based on hyperspectral reflectance information, which is used to guide a laser of a Raman spectroscopy unit to those ROI, and second to classify AD-associated pathology from the Raman spectra returned from interrogation of these particular ROI and from the hyperspectral reflectance information. Taken together, these two optical spectroscopy modalities and the machine learning algorithm result in a high-sensitivity, high-specificity, non-invasive device for pre-screening at-risk populations for AD, diagnosis, and of tracking treatment and intervention efficacy.

In some examples, the machine learning algorithm is trained using verified training data. The verified training data can be obtained by comparing adjacent slices of ex vivo tissue samples from subjects that are known to have had AD. One slice of the tissue of a subject is analyzed using hyperspectral imaging and Raman spectroscopy, and an adjacent slice is stained and verified through histology using a microscope or other imaging modalities. When an AD pathology is verified using histology on one slice, the adjacent slice can be analyzed at the corresponding location using hyperspectral imaging and the Raman spectroscopy, which can therefore be used as verified training data for the machine learning algorithm.

A non-invasive in vivo ocular light-based detection device for detection of one or more AD-associated pathologies from an eye of a subject, comprising: a hyperspectral reflectance imaging unit that includes a broadband light source and a hyperspectral camera; a Raman spectroscopy unit that includes a laser and a spectrometer; memory; and one or more processors configured to execute instructions stored in the memory to: control the hyperspectral reflectance imaging unit to illuminate a wide field-of-view of a fundus of the eye using the broadband light source, and detect resulting reflected and/or backscattered light from the eye using the hyperspectral camera for determining hyperspectral reflectance information, determine one or more ROI from the hyperspectral reflectance information as being a potential AD-associated pathology, control the Raman spectroscopy unit to illuminate each of the one or more ROI using the laser, and detect Raman scattered light from the eye resulting from the laser and using the spectrometer for determining Raman spectroscopy information, and classify, using the hyperspectral reflectance information and the Raman spectroscopy information, the subject as having one or more AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

Another example embodiment is a method of non-invasive in vivo detection of one or more AD-associated pathologies from an eye of a subject, comprising: controlling a hyperspectral reflectance imaging unit to illuminate a wide field-of-view of a fundus of the eye using a broadband light source; detecting light from the eye resulting from the broadband light source using a hyperspectral camera for determining hyperspectral reflectance information; determining, using one or more processors, a location of one or more ROI from the hyperspectral reflectance information as being a potential AD-associated pathology; controlling a Raman spectroscopy unit to illuminate each of the one or more ROI using a laser; detecting Raman scattered light from the eye resulting from the laser using a spectrometer for determining Raman spectroscopy information; and classifying, using the one or more processors, using the hyperspectral reflectance information and the Raman spectroscopy information, the subject as having one or more AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

Another example embodiment is a computer program product by a machine learning training process, the computer program product comprising instructions stored in a non-transitory computer readable medium which, when executed by a computer, causes the computer to carry out non-invasive in vivo detection of one or more Alzheimer's Disease (AD)-associated pathologies from an eye of a subject, the machine learning training process comprising: training, using one or more processors, the computer program using verified training data, the verified training data obtained by: slicing an ex vivo tissue sample from a subject into tissue slices, placing the tissue slices onto slides, staining a first tissue slice of a first slide, providing a second slide having a second tissue slice that was adjacent to the first tissue slice in the tissue sample and is unstained, verifying that the stained first tissue slice has one or more of the AD-associated pathologies using histology, performing at least one imaging modality on the second slide to obtain imaging information, and classifying the imaging information as one or more of the AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

Another example embodiment is a method for machine learning training of a computer program stored in a memory which, when executed by a computer, causes the computer to carry out non-invasive in vivo detection of one or more AD-associated pathologies from an eye of a subject, the method comprising: training, using one or more processors, the computer program using verified training data, the verified training data obtained by: slicing an ex vivo tissue sample from a subject into tissue slices, placing the tissue slices onto slides, staining a first tissue slice of a first slide, providing a second slide having a second tissue slice that was adjacent to the first tissue slice in the tissue sample and is unstained, verifying that the stained first tissue slice has one or more of the AD-associated pathologies using histology, performing at least one imaging modality on the second slide to obtain detection information, and classifying the detection information as one or more of the AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein; and storing the trained computer program to the memory.

BRIEF DESCRIPTION OF THE DRAWINGS

Reference will now be made, by way of example, to the accompanying drawings that show example embodiments, in which:

5

Figure 1:
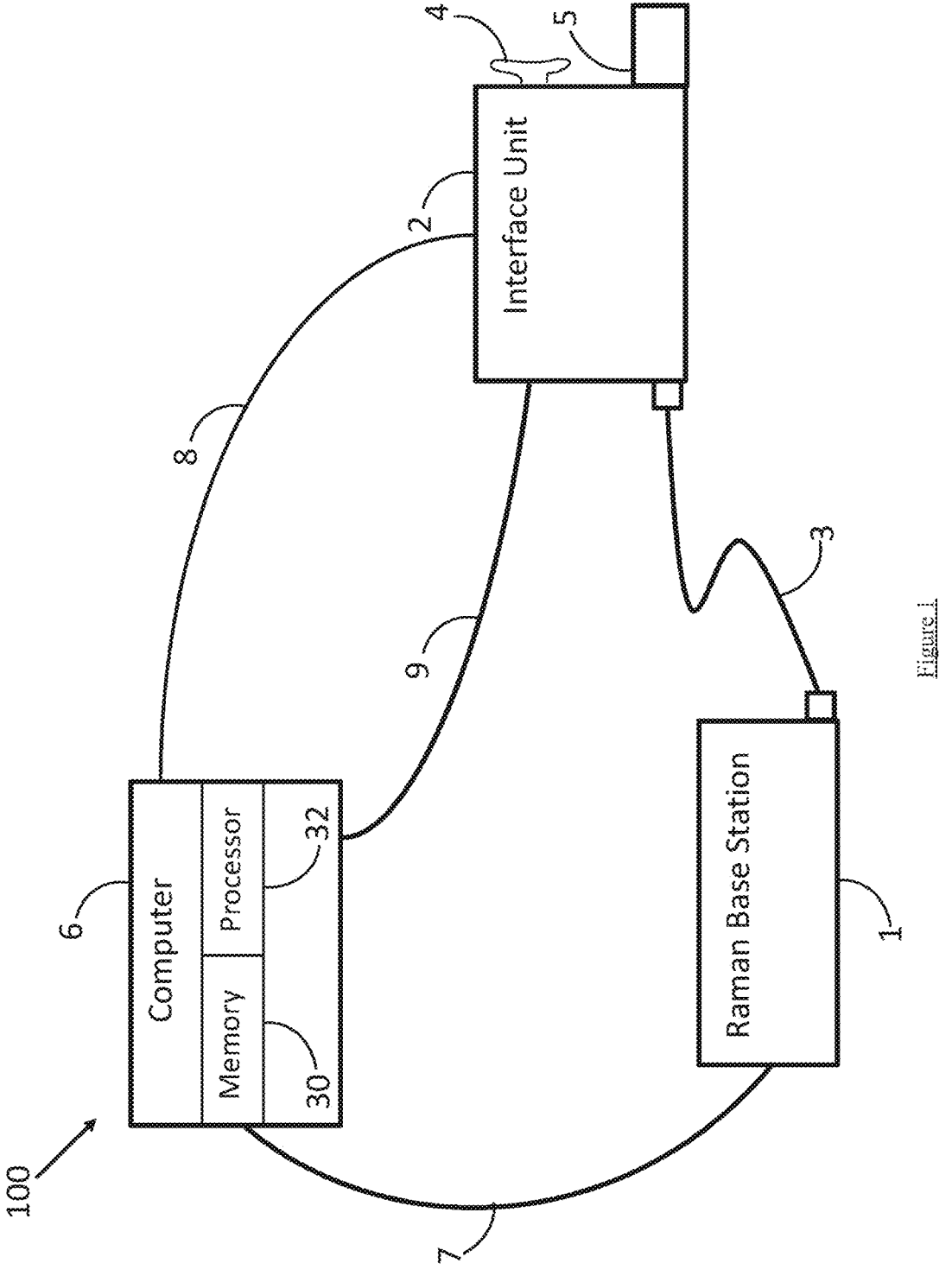

FIG. 1 illustrates in schematic form a non-invasive ocular light-based ocular detection device for detecting AD pathologies in the eye, in accordance with an example embodiment.

Figure 2:
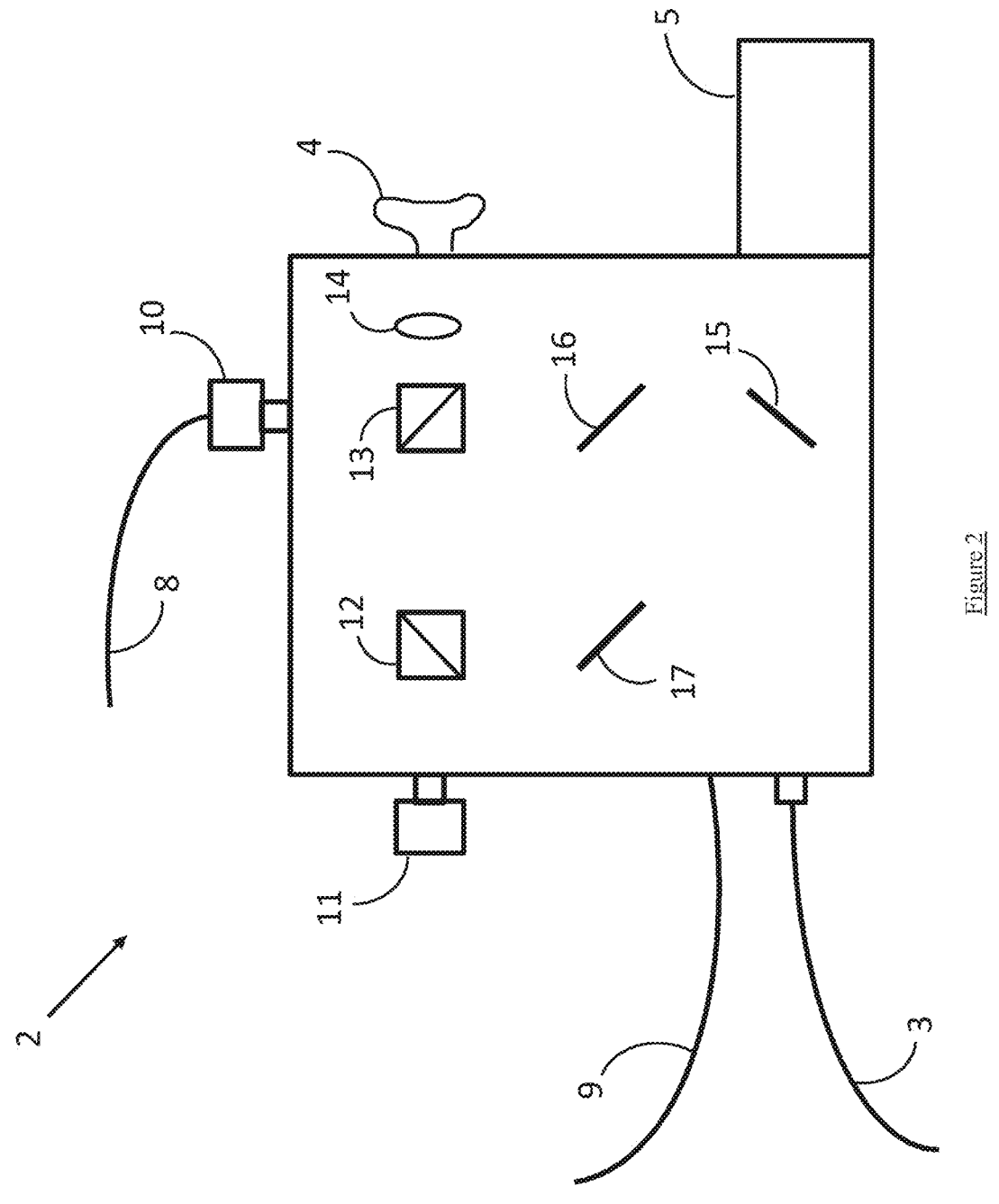

FIG. 2 illustrates a side schematic view of an interface unit of the device of FIG. 1.

Figure 3:
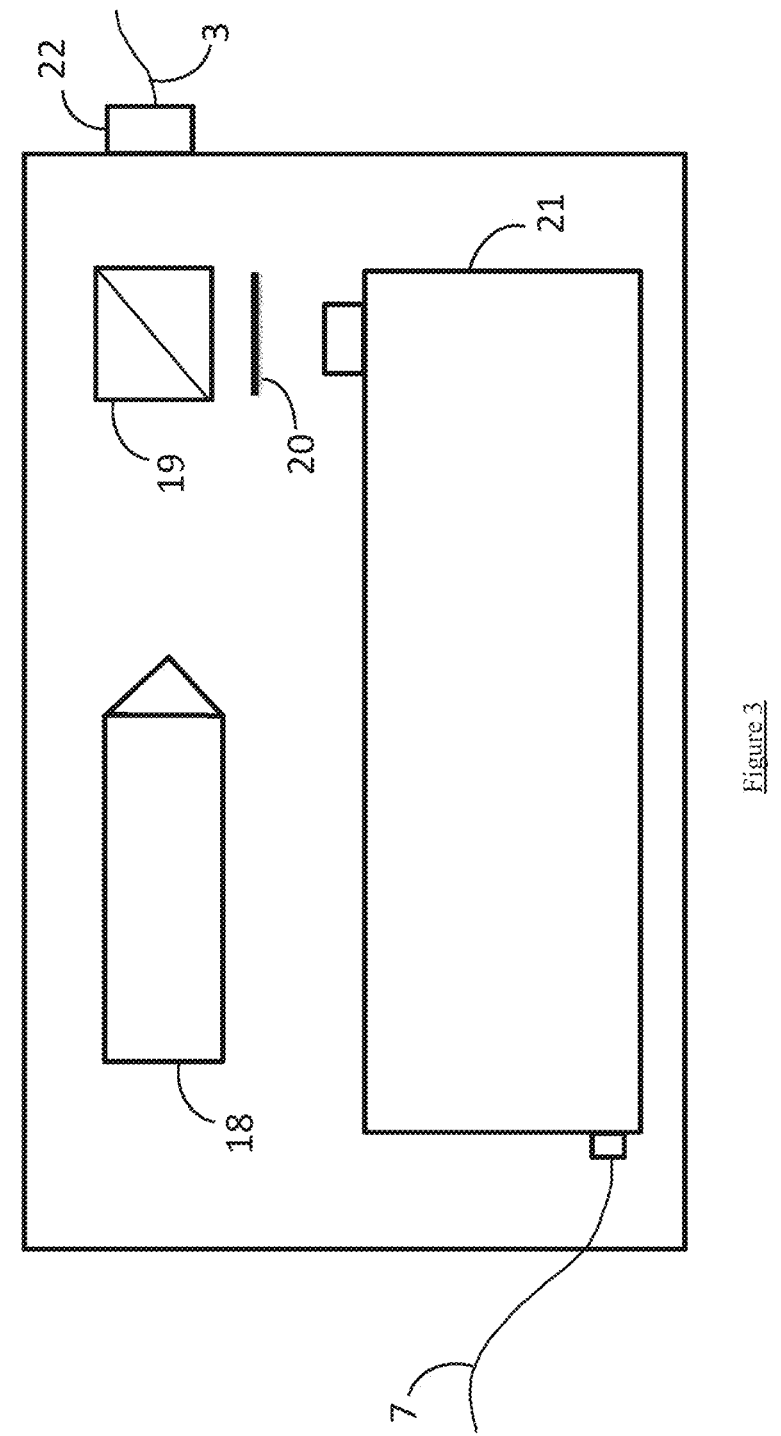

FIG. 3 illustrates a top-down schematic view of a Raman spectroscopy unit of the device of FIG. 1.

Figure 4:
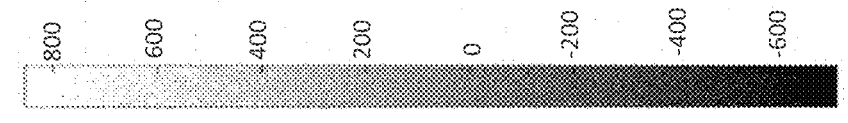
Figure 4:
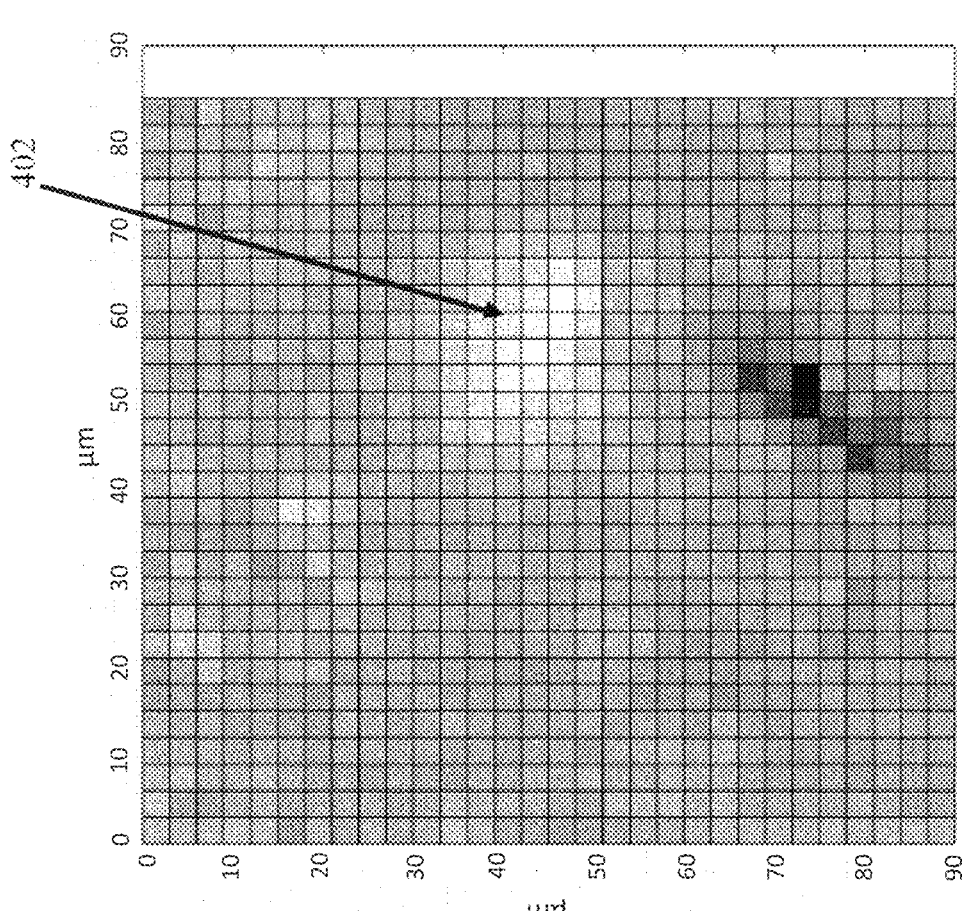

FIG. 4 shows a Raman map of unstained, formalin fixed, paraffin embedded (FFPE) brain tissue from a post-mortem AD patient.

Figure 5:
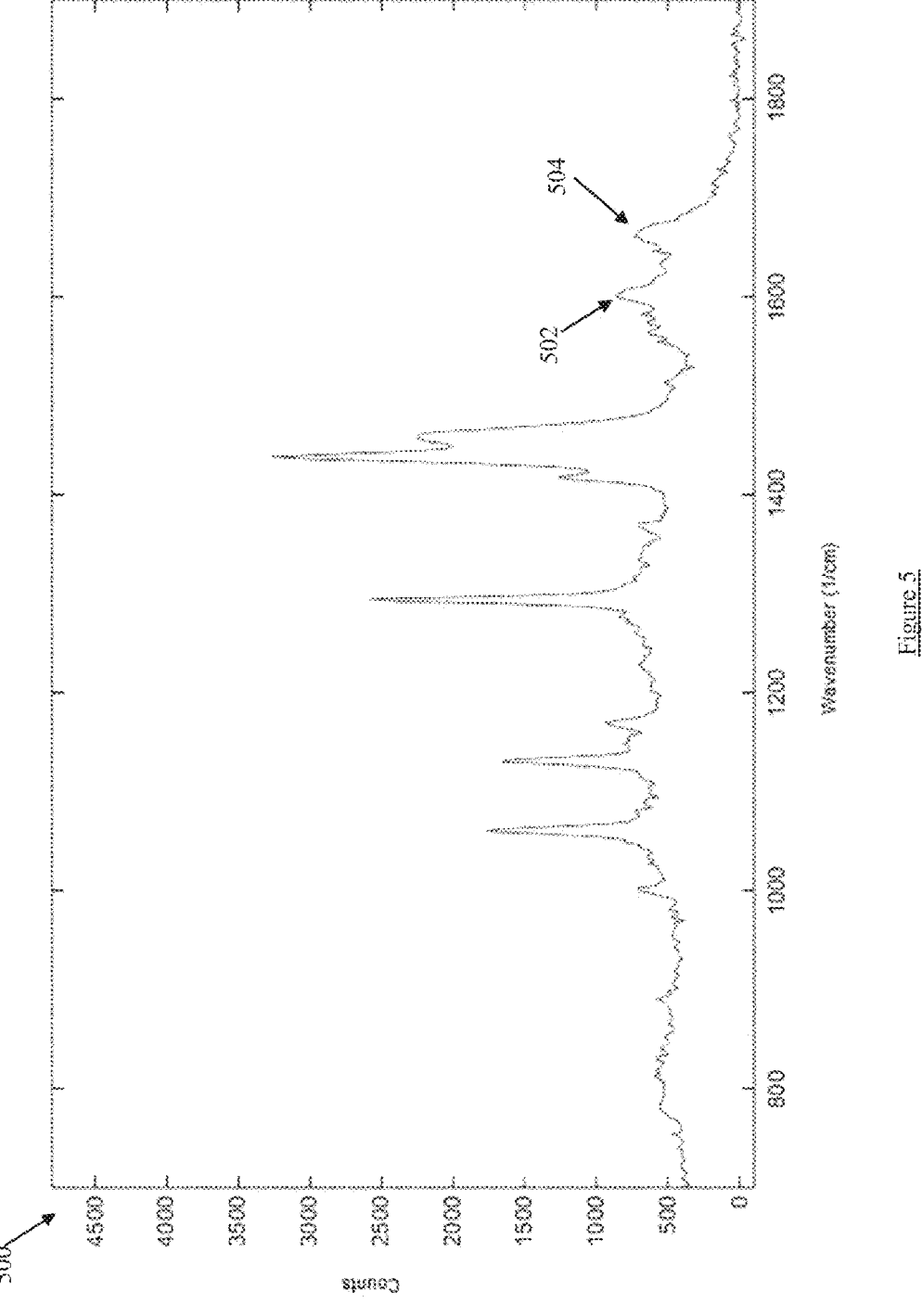

FIG. 5 shows a broadband Raman spectrum of an AD plaque, corresponding to a pixel from the Raman map of FIG. 4.

Figure 6:
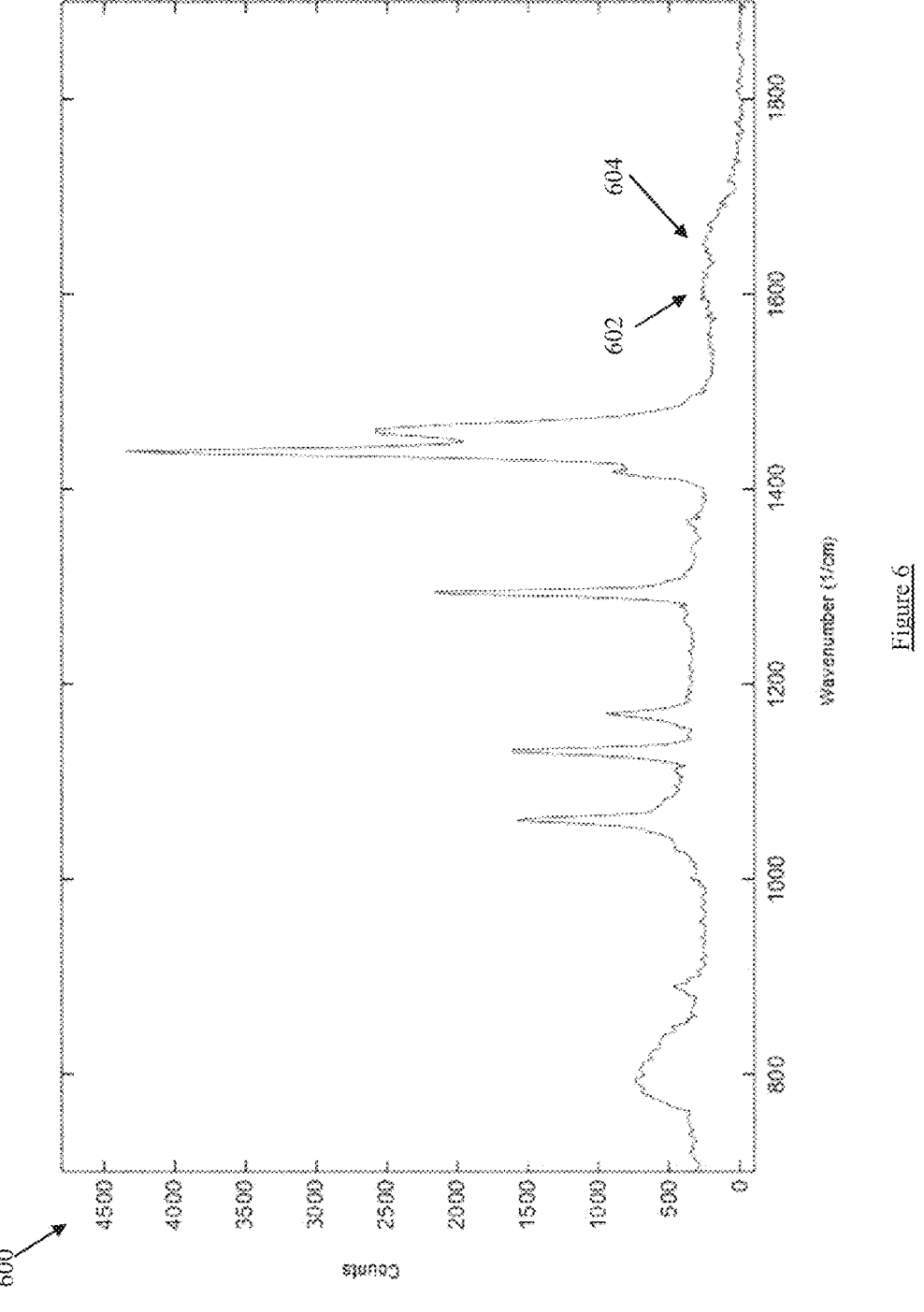

FIG. 6 shows a broadband Raman spectrum of a pixel from the Raman map of FIG. 4 containing background tissue.

Figure 7:
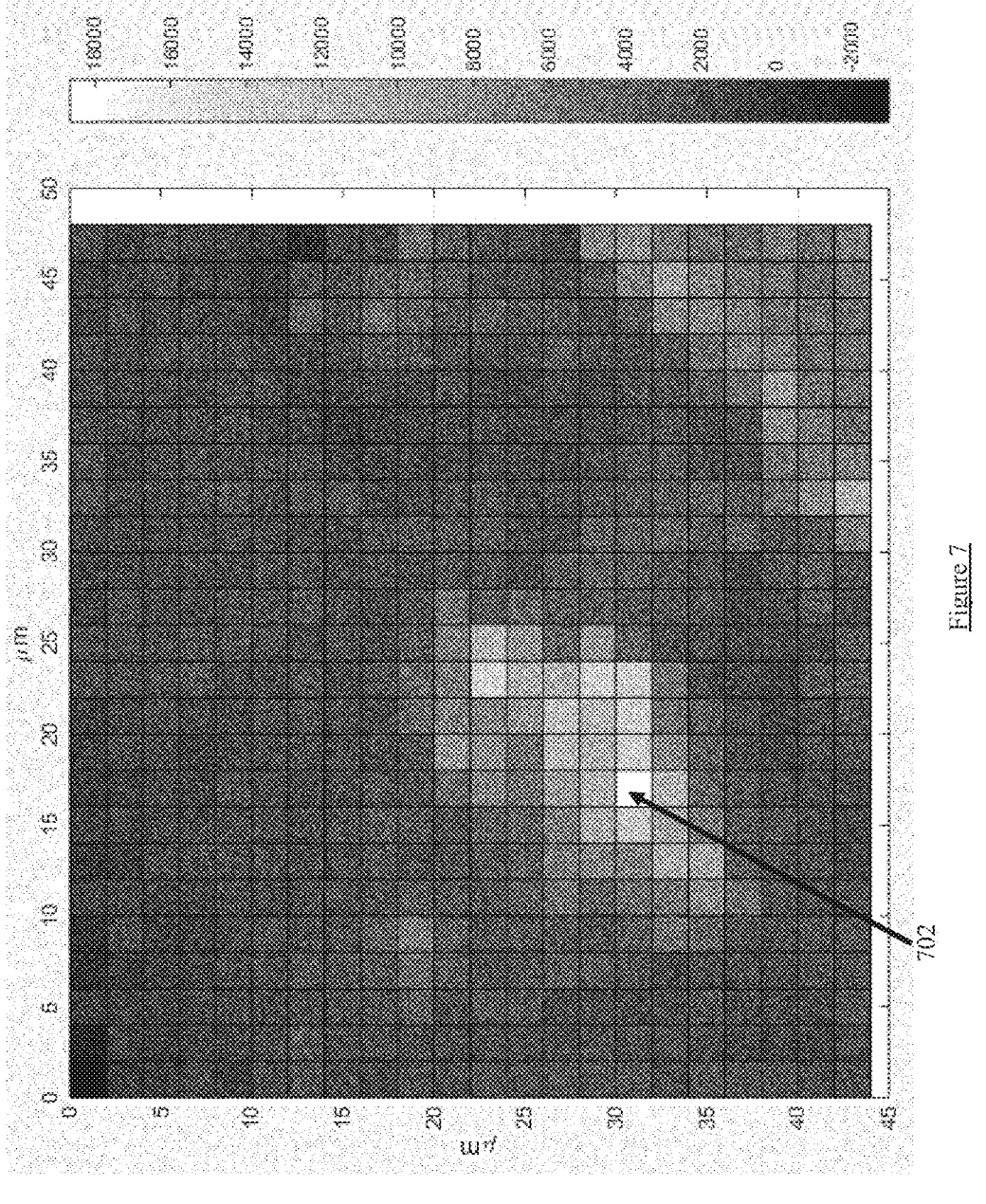

FIG. 7 shows another Raman map of unstained, FFPE brain tissue from a post-mortem AD patient.

Figure 8:
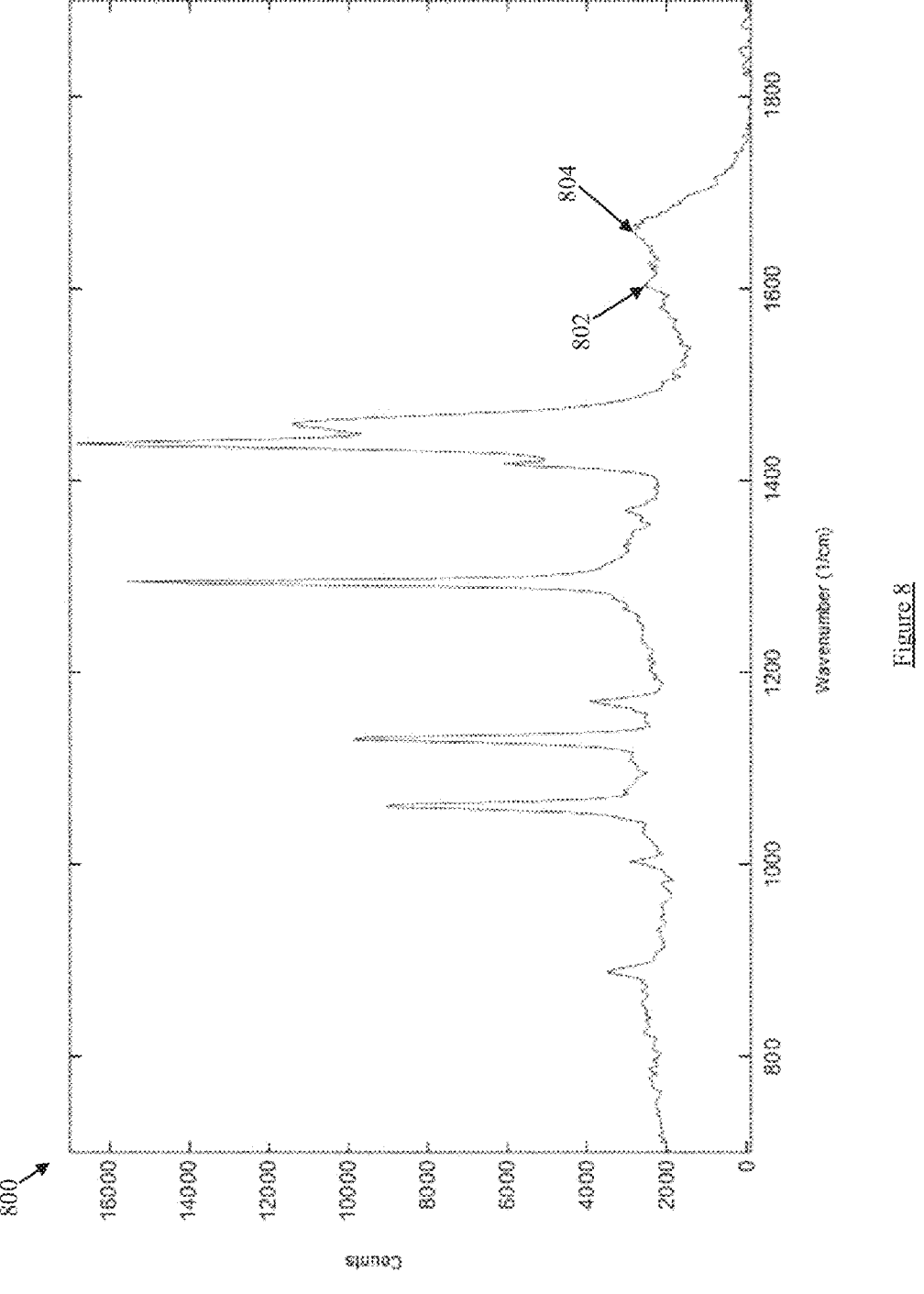

FIG. 8 shows a broadband Raman spectrum corresponding to a pixel from the Raman map of FIG. 7.

Figure 9:
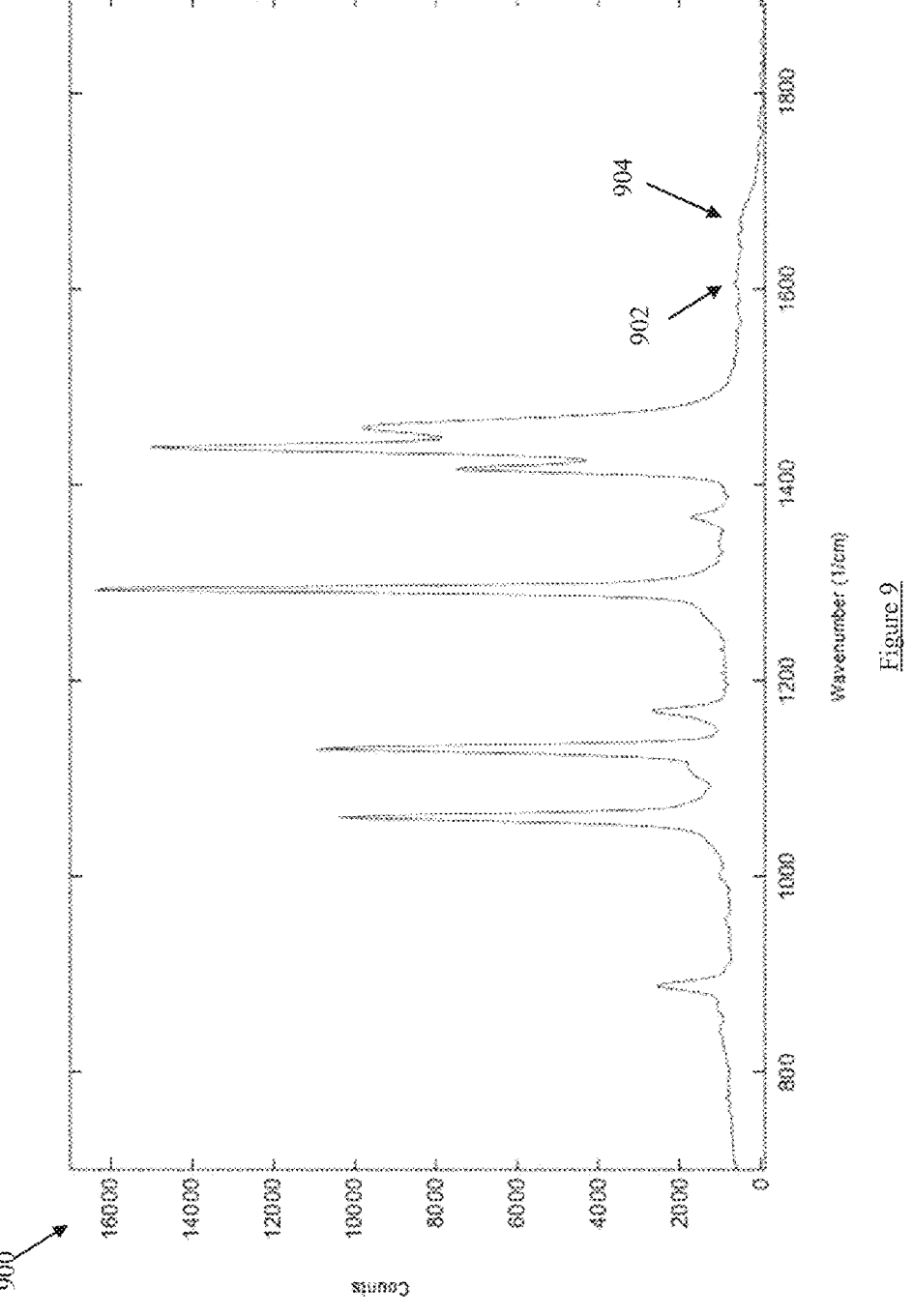

FIG. 9 shows a broadband Raman spectrum of a pixel from the Raman map of FIG. 7 containing background tissue.

Figure 10:
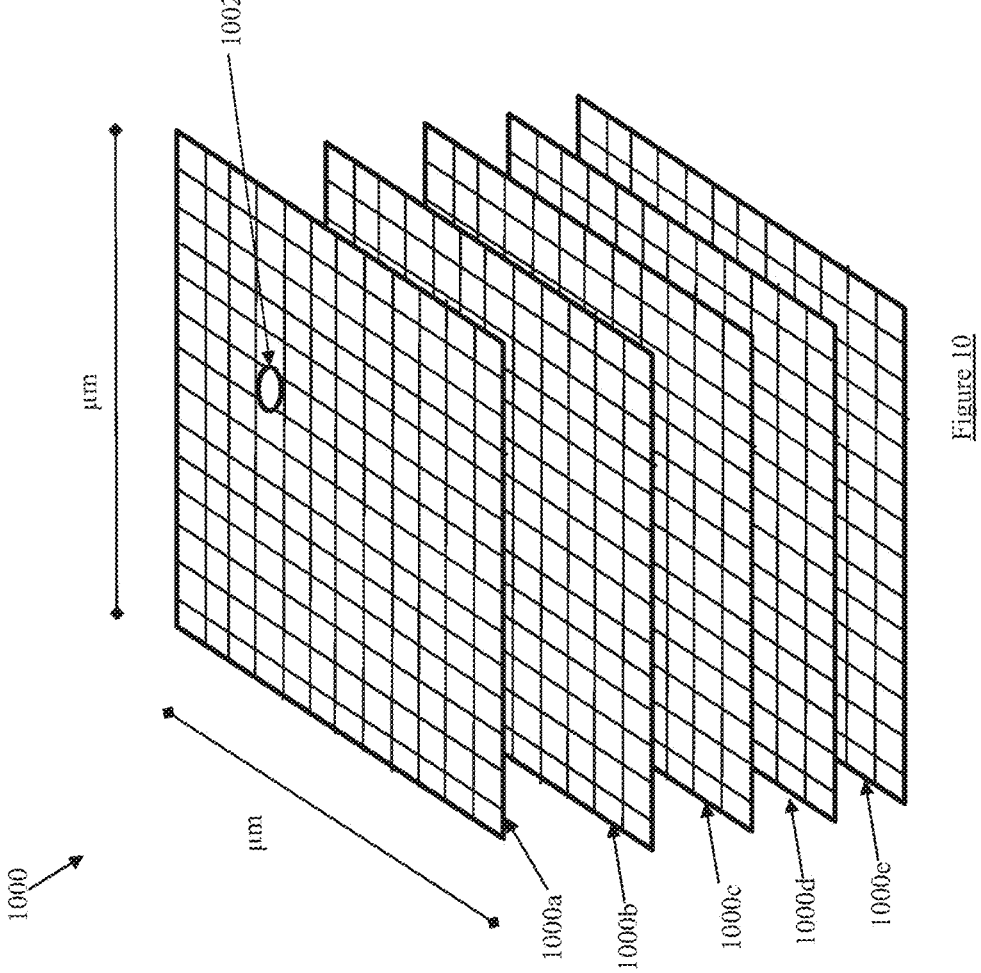

FIG. 10 illustrates hyperspectral imaging maps of patient tissue for identifying regions of interest for subsequent Raman spectroscopy, in accordance with an example embodiment.

Figure 11:
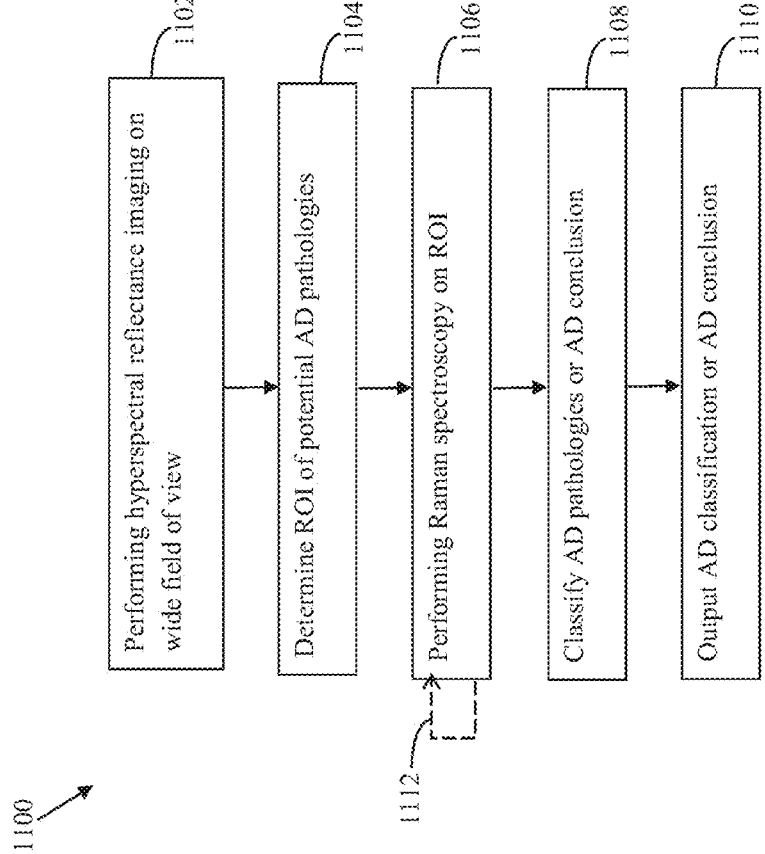

FIG. 11 illustrates a flow diagram of a method for detecting AD pathologies in the eye, in accordance with an example embodiment.

Figure 12:
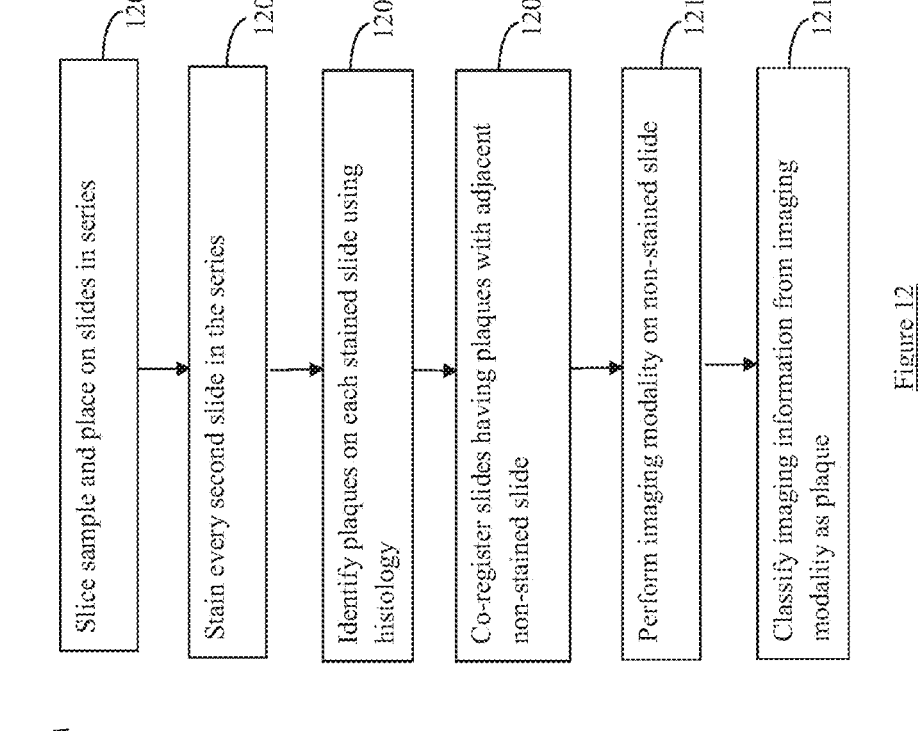

FIG. 12 illustrates a flow diagram of a method for determining training data for a machine learning algorithm of the device of FIG. 1, in accordance with an example embodiment.

Figure 13:
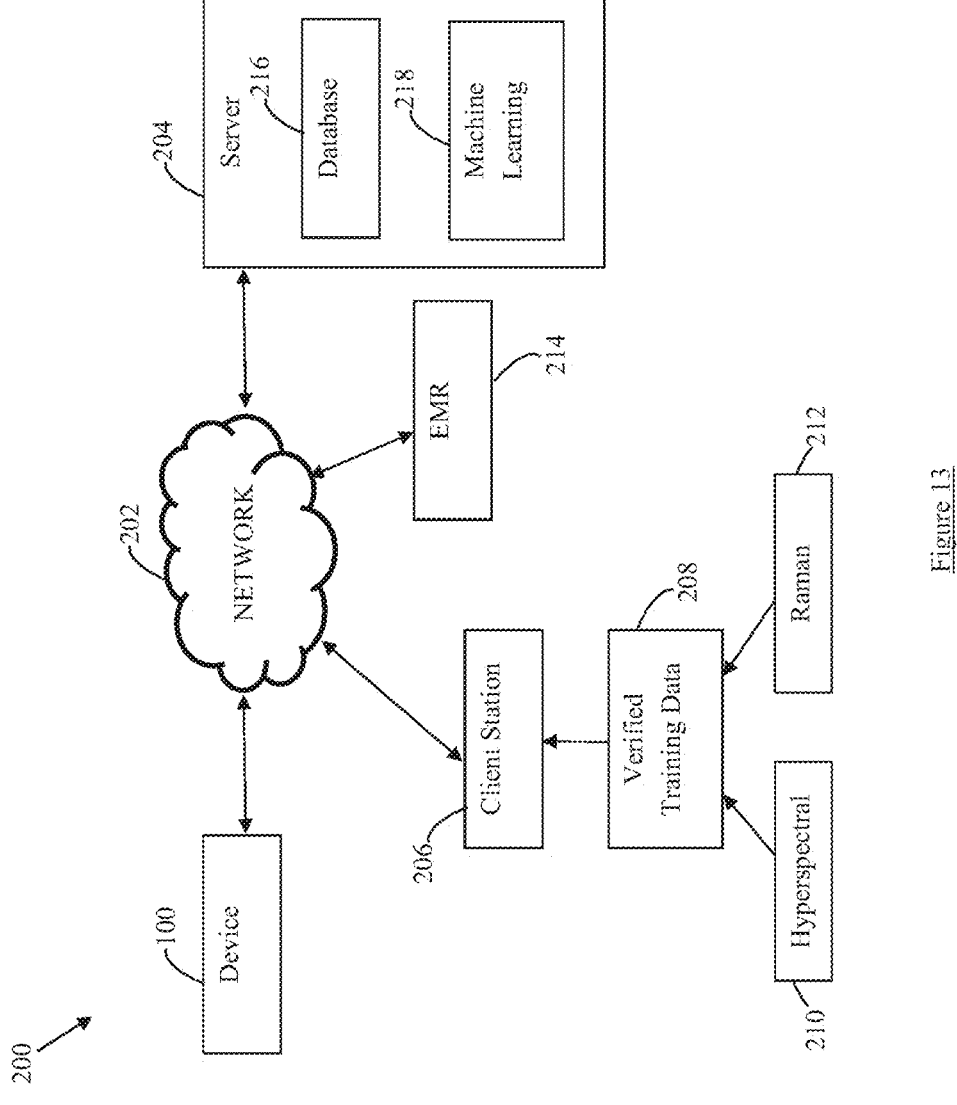

FIG. 13 illustrates a system for detecting AD pathologies in the eye, in accordance with an example embodiment.

Figure 14:
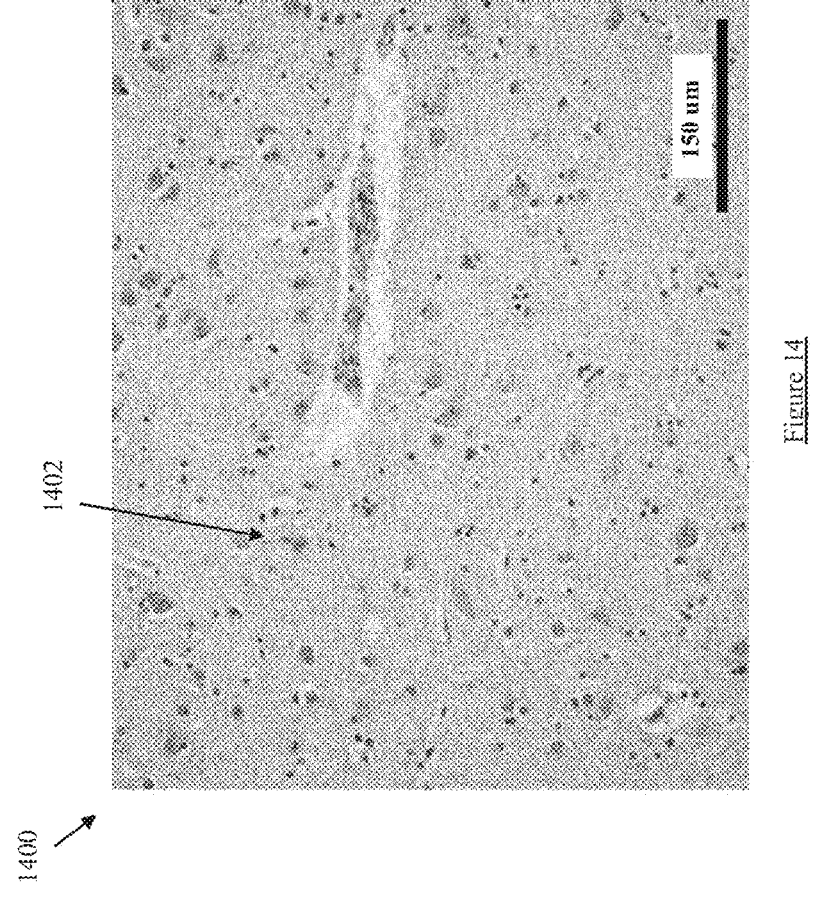

FIG. 14 illustrates a polarization microscopy image that includes a plaque (e.g. a stained red spot), corresponding to the Raman map of FIG. 4.

Figure 15:
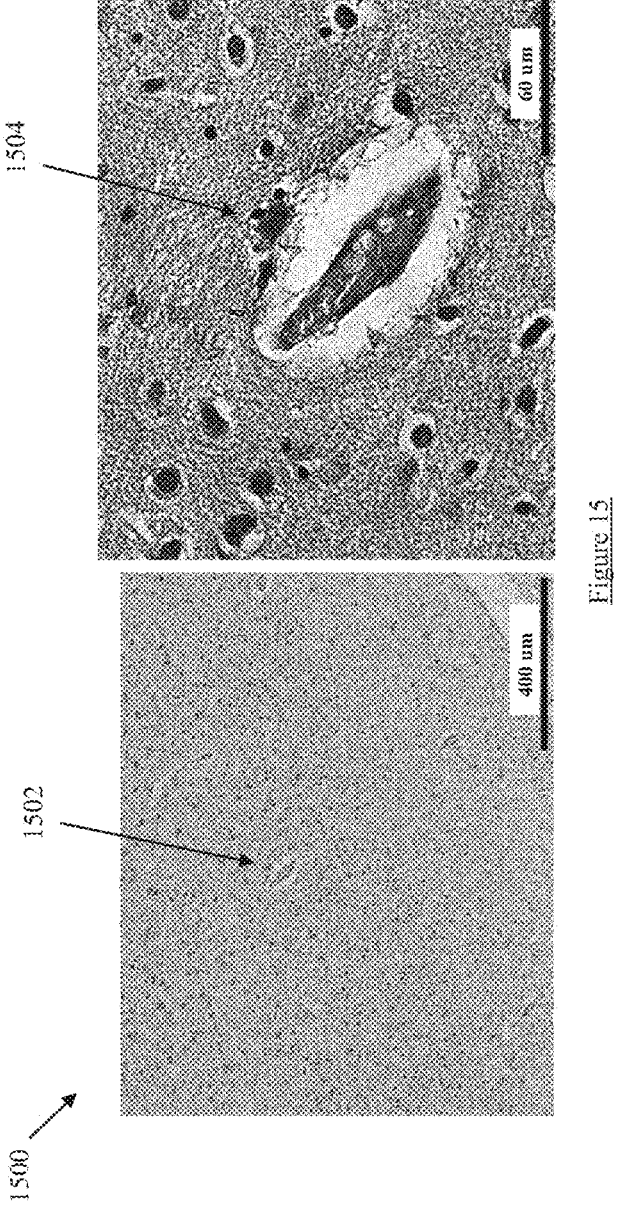

FIG. 15 illustrates two different magnifications (10×, left and 40×, right) of polarization microscopy images of a stained slide, showing a plaque next to a vessel, corresponding to the Raman map of FIG. 7 (mirror image).

Figure 16:
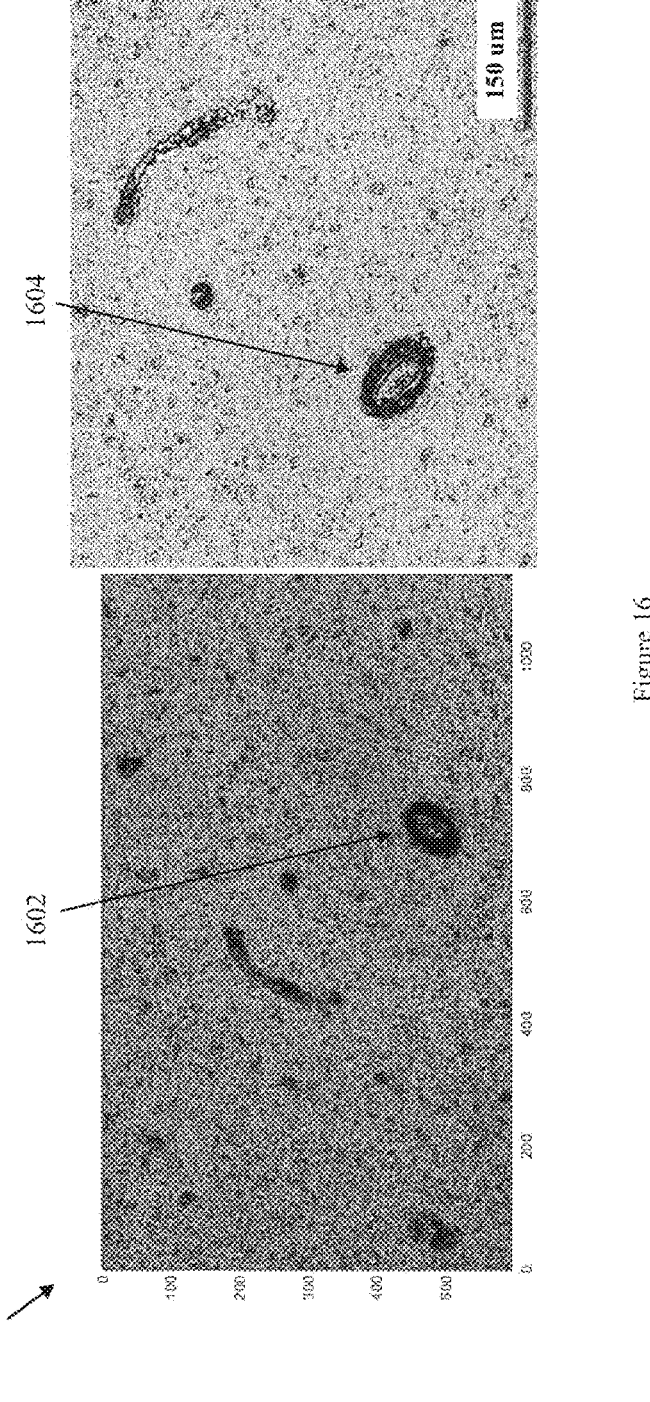

FIG. 16 illustrates a hyperspectral image of an unstained slide (left), containing the same vessel as seen in FIG. 15 in an adjacent slice, and a polarization microscopy image of same (right, mirror image).

Figure 17A:
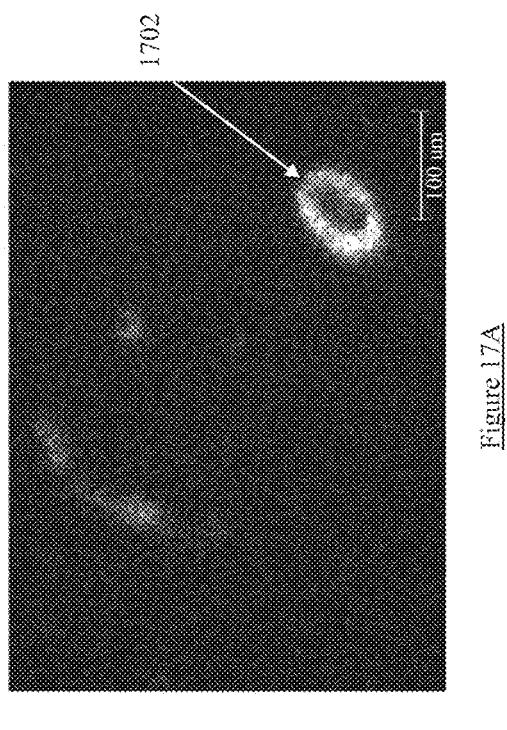

FIG. 17A illustrates a white light image of the same unstained slide of FIG. 16, taken by a Raman spectroscopy unit, which shows that the same vessel of FIG. 16 can be located using the Raman spectroscopy unit.

Figure 17B:
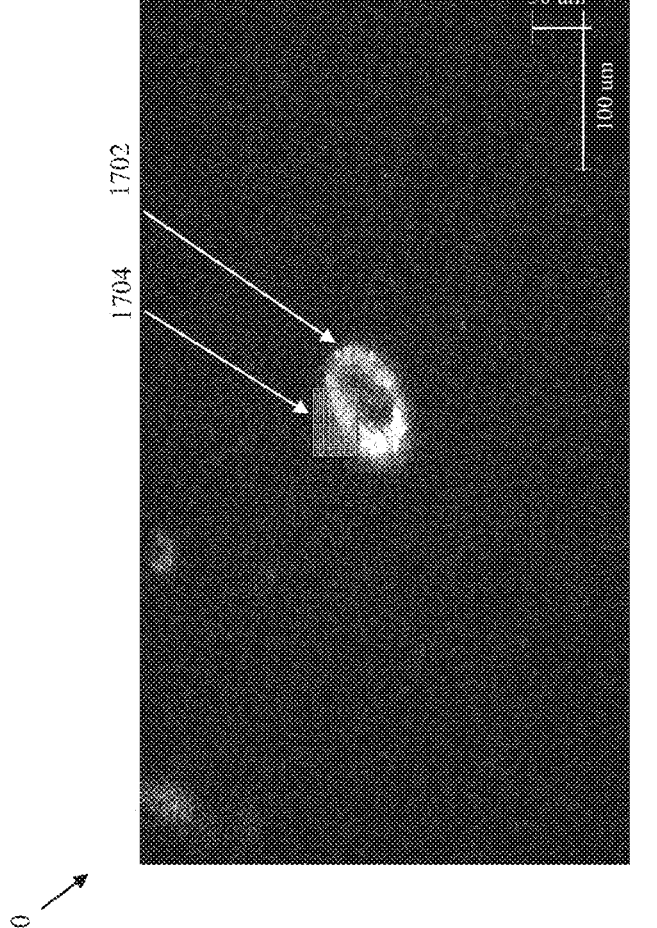

FIG. 17B illustrates the white light image of FIG. 17A, showing a region that has been Raman mapped.

Similar reference numerals may be used in different figures to denote similar components.

DETAILED DESCRIPTION OF EXAMPLE EMBODIMENTS

FIG. 1 illustrates a non-invasive ocular in vivo light-based detection device 100 for detecting AD-associated patholo-gies in the eye, in accordance with an example embodiment. The device 100 can be used to perform optical detection of part of the fundus, such as the retina. The device 100 is a point-of-care (POC) tool that provides an accessible and noninvasive procedure for identifying at-risk populations of

6

AD. The device 100 detects light reflected off of the fundus from a broadband light source. The device 100 can also detect Raman scattered light emitted from the fundus in response to interrogation by a monochromatic laser, in order for the device 100 to detect the presence of one or more AD-associated pathologies with high specificity. This allows for the identification of at-risk populations based on the presence of one or more AD-associated pathologies.

The device 100 includes a Raman base station 1 and an interface unit 2 which interfaces with the subject under study. The subject can be human or animal, for example. The device 100 includes a hyperspectral reflectance imaging unit and a Raman spectroscopy unit. The hyperspectral reflec-tance imaging unit is in the interface unit 2. The Raman spectroscopy unit is defined by the Raman base station 1 and components of the interface unit 2.

The subject is positioned in front of the interface unit 2, against a rubber eye cup 4 with their chin resting on a chin rest 5. The Raman base station 1 and the interface unit 2 are connected via an optical fiber 3, which serves to deliver monochromatic laser light in a narrow beam arrangement from the Raman base station 1 to the interface unit 2. The laser light can be 532 nm coherent light in one example, or 785 nm in another example. Other laser wavelengths can be used in other examples. Through the same interface unit 2, the optical fiber 3 also collects light that is re-emitted by a specific region or part of the subject's eye in response to laser excitation, due to a Raman process, and delivers this re-emitted light back to the Raman base station 1, for detection by a suitable photodetector (e.g. spectrometer). In other example embodiments, the Raman base station 1 and the interface unit 2 may be combined into a single device or further separated, as would be apparent to one of ordinary skill in the art in view of the teachings herein. A computer 6 is used to interface (control and communicate) with the Raman base station 1 and the interface unit 2. The computer includes a memory 30 and a processor 32. An electrical cable 7 relays information to and from the Raman base station 1 and the computer 6, and a coaxial cable 8 relays information to and from the interface unit 2 and the com-puter 6. The computer 6 processes received information using a machine learning algorithm, described in greater detail herein. The computer 6 sends the output of the machine learning algorithm or other control information over electrical cable 9 to the interface unit 2, which uses the received information to steer the laser light from the optical cable 3 to specified regions or parts of the subject's eye. In an example, the computer 6 can include one or more image analysis dedicated chips (e.g., graphics processing units or GPUs) that can decompose the received imaging informa-tion and partially or wholly process the imaging information in real-time.

FIG. 2 illustrates the interface unit 2 in greater detail. The interface unit 2 can include one or more controllers or processors (not shown) for controlling operation of the interface unit 2 and for communicating with the computer 6 and the Raman base station 1. The target under study can be placed in front of a rubber eye cup 4. In the case of in vivo imaging, the subject will place their eye against the eye cup 4 and rest their chin on the chin rest 5. This serves to align the subject with the optical path of the interface unit 2. The interface unit 2 can also be used for in vivo imaging of an animal, ex vivo imaging of tissues, or any other suitable target, wherein a stage may be attached to the interface unit so as to position the target in a suitable position (e.g. the focal plane of the optical system). Other components for supporting and positioning of the target may be used in other examples.

The interface unit 2 may include a fundus camera, or similar, which is capable of wide field-of-view imaging of the fundus of the subject. A light sensor 10, capable of detecting and discriminating different wavelengths of light, is used to capture the image. The light sensor may take the form of a hyperspectral camera, multispectral camera, red-green-blue color camera, or monochromatic camera. A broadband light source 11 covering the visible and near-infrared spectrum (400 nm-1100 nm) is used to illuminate the subject's retina, in an example. The broadband light source 11 passes through two beam splitters 12 and 13 and is directed onto the retina via focusing elements, such as a lens assembly 14. It will be appreciated that, in other example embodiments, other focusing and beam shaping elements may be present to tailor the light distribution on the subject's eye. Once directed onto the subject's eye, at least some of the broadband light is reflected and/or backscattered from the retina, or other region of the eye. A portion of this light travels back into the interface unit 2 where it is collected by the lens assembly 14 and directed by beam-splitter 13 to the hyperspectral camera 10. Other suitable configurations for the location of the hyperspectral camera 10 and the geometry of collecting the reflected and/or backscattered light will be apparent to one of ordinary skill in the art.

The entire field of view, as dictated by the lens assembly 14, is detected by the light sensor 10 in a single capture. For example, in the case of the hyperspectral camera 10, all wavelength information is detected across the entire field of view simultaneously. The wide field-of-view hyperspectral reflectance imaging unit contrasts with raster scanning over rows or columns of the entire field of view, or with detecting one wavelength band at a time (e.g., multispectral imaging), or line hyperspectral cameras, or the illuminating light requiring coherence (e.g., optical coherence tomography).

In this example, the central area of the subject's retina is the imaging target filling the entire field of view. Other regions of the fundus can serve as the imaging target in other examples.

A co-axial cable 8 sends the hyperspectral information detected by the hyperspectral camera 10 to the computer 6 for processing in real time. As described in greater detail herein, a machine learning algorithm of the computer 6 uses this hyperspectral information to ascertain a location and size of one or more ROI based on previously acquired training data. In some examples, the size of each ROI can be defined as the circular area centered on the location (e.g., indicated by radius or diameter) or as a rectangular area (e.g. indicated by M×N pixels). Once the one or more ROI have been identified, another imaging modality can be performed by the device 100, for example Raman spectroscopy using the Raman spectroscopy unit. A second light source, such as a monochromatic laser 18 (FIG. 3), is housed inside the Raman spectroscopy unit. Light from the monochromatic laser 18 is steered to the appropriate ROI by mirrors 15, 16, 17. The mirrors 15, 16, 17 are controlled using electro-mechanical motors by the interface unit 2 so as to steer the focused laser light onto the appropriate ROI of the subject's retina, as identified prior from the hyperspectral information obtained by the hyperspectral reflectance imaging unit. Electrical cable 9 carries the signal from the computer 6 to the interface unit 2 to control the angle of the mirrors 15, 16, 17. The laser light interacts with the retina at the ROI and, via a Raman phenomenon, light is Raman scattered with a specific wavenumber shift or shifts that are characteristic of the chemical constituents of the interrogated tissue. This re-emitted light is collected via the lens assembly 14, transmitted through beam-splitter 13 and then reflected by beam-splitter 12 and mirrors 15, 16, 17, before being coupled back into the optical fiber 3. The optical fiber then transmits this re-emitted, Raman light back to the Raman base station 1 for detection.

Raman spectroscopy can be performed on each of the identified ROI, to identify the presence or absence of a wavenumber shift or shifts that are characteristic of one or more specified chemical constituents. By Raman spectroscopy using the mechanical mirrors 15, 16, 17, the lens assembly 14 and/or the diaphragm, the spectral information of the ROI can be obtained by the computer 6, which can comprise one or more specific pixels in the tissue environment. In some examples, the counts at a particular wavelength are detected, and the wavenumber shift or shifts is calculated therefrom by calculating a difference from the known wavelength of the monochromatic laser 18.

In an example, the Raman spectroscopy information of each identified ROI having the location and size can be detected in a single capture by the Raman spectroscopy unit, and stimulated by one instance of the monochromatic laser 18 at the location and size of the ROI. In an example, the lens assembly 14 can be used to control the size of the ROI that is to be stimulated by the laser light from the monochromatic laser 18 of the Raman spectroscopy unit so that the Raman spectroscopy information of the entire ROI is detected single capture. In some examples, a diaphragm, iris or collimation device (not shown) can also be used to control the size of the ROI that is stimulated by the monochromatic laser 18.

In another example, each pixel of the ROI is scanned by each pixel being stimulated by the monochromatic laser 18 and Raman spectroscopy information is acquired by Raman spectroscopy unit over each pixel of the ROI to create a Raman map of the ROI or to calculate integrated spectroscopy results over the ROI. It would be appreciated that the entire wide field of view of the retina does not need to be Raman scanned.

In various examples, described in greater detail herein, for the Raman spectroscopy unit an optical filter 20 (FIG. 3) can be used to pass through a specific wavelength or band of interest prior to detection by the Raman spectroscopy unit. As well, digital filtering can be performed by the computer 6 to a specific wavelength or band of interest.

The operation of the hyperspectral camera 10 for performing the hyperspectral imaging will now be described in greater detail. The hyperspectral camera 10 includes a 2-dimensional array of light sensors, identified by pixels, that are sensitive to light in the visible and near-infrared range. A 2-dimensional filter array is placed on top of this array of light sensors. Each individual filter within the 2-dimensional filter array selectively transmits light of a given wavelength, which is then detected by a dedicated pixel in the sensor array. A pattern of the filter array is repeated across the entire light sensor so that light from every point in the field of view is filtered and detected by the sensor. In this way, all wavelength/frequency information, from every region of the field of view, is captured simultaneously in a single capture. This differs from line hyperspectral cameras, which can only detect and discriminate different wavelengths of light across a 1-dimensional line within the field of view. This also differs from typical multispectral approaches, which use multiple filters in sequence to capture wavelength information, i.e., first capturing the 'red' information, then inserting a different filter to capture the 'green' information, and so on.

FIG. 3 illustrates in greater detail an example embodiment of the Raman base station 1. A monochromatic laser 18 within the visible or near-infrared wavelength range is housed inside the Raman base station 1. The laser 18 delivers 532 nm coherent light in an example, or 785 nm in another example. The laser 18 can emit other specific wavelengths in other examples. The laser output from the laser 18 is directed through beam splitter 19 and coupled into an optical fiber 3 through a fiber adapter 22. The optical fiber 3 transmits the laser light to the interface unit 2. As described above, the interface unit 2 directs this laser light onto each ROI of the subject's retina (as identified by the computer 6 based on the hyperspectral imaging). In an example, the size (radius) of the laser light onto each ROI can be controlled using the lens assembly 14 and/or the diaphragm. In other examples, the laser light scans each ROI pixel-by-pixel. The laser light interacts with the tissue at these regions and, via a Raman phenomenon, light is scattered from the tissue with a change in wavelength that is characteristics of the interrogated tissue. This Raman scattered light is shaped and directed by collection optics, such as one or more further lenses (not shown), so that it may be efficiently coupled into an optical fiber 3 and brought back into the Raman base station 1. Beam splitter 19 serves to re-direct this returning light into a spectrometer 21 for detection. An optical filter 20 can comprise a long-pass filter with cut-off at 534 nm (greater than the laser wavelength from the laser 18), is used to remove any direct laser light that underwent back-reflection along the optical path and found its way back to the Raman base station 1. In another example, the optical filter 20 can comprise a notch filter with a narrow filter against the specific wavelength of the laser (e.g., 532 nm coherent light in one example, or 785 nm in another example). The optical filter 20 ensures that only light from a Raman phenomenon is detected by the spectrometer 21, and that light from the original laser 18 is removed by the optical filter 20. The spectrometer 21 comprises a refracting element to separate individual wavelength components and project these components onto distinct pixels in a light sensor. The spectral information measured by the spectrometer 21 is then sent to the computer 6 via electrical cable 7 for further processing. The computer 6 can perform further filtering algorithmically (digital filtering), as an alternative or in conjunction with the physical optical filter 20. The Raman base station 1 can include one or more controllers or processors (not shown) for controlling operation of the Raman base station 1 and for communicating with the computer 6 and the interface unit 2.

In some examples, the illumination and light collection systems may be performed by using Adaptive Optics (AO) systems and methods.

The machine learning algorithm, trained on Raman spectra of one or more substances, is then executed by the computer 6 to identify a specific wavenumber shift or shifts that are characteristic of the chemical constituents of the source of the Raman signal, thereby specifically identifying the presence of protein aggregates or other pathologies related to AD in the eye. The identifying can include counting instances of the wavenumber shift or shifts, and/or other mathematical formulas. Example protein aggregates of the fundus that can be detected by the device 100 include Tau neurofibrillary tangles (e.g., soluble or insoluble Tau oligomers or Tau fibrils), Amyloid Beta deposits (e.g. soluble Amyloid Beta aggregates or insoluble Amyloid Beta plaques, Amyloid Beta oligomers or Amyloid Beta precursors), and Amyloid precursor protein (APP). Detection of this Raman signal allows for much higher specificity for detection of AD-associated pathologies than compared to hyperspectral imaging alone. AD-associated pathologies can also be tracked over time, wherein comparison of Raman spectroscopy information taken from the same patient at different times are compared to assess the classification of AD pathology or other AD conclusions. For example, Raman count values (or ratios or other characteristics) of a potential plaque at a particular ROI may increase over time in an AD subject. In some examples, the machine learning algorithm uses both the Raman spectroscopy information and the hyperspectral reflectance information to better classify the AD-associated pathology or other AD-associated conclusions.

The computer 6 can interpret the Raman spectroscopy information and use the machine learning algorithm to classify the ROI as containing or not containing one or more AD-associated pathologies, such as protein aggregates. In example embodiments, the classification of the subject can also be an AD conclusion as to whether: the subject has AD, or a precursor to AD, or is pre-screened for potential AD and requires further investigation. The computer 6 can be programmed to output the classifications to a display screen, store to local memory, or transmit to another device such as server 204, client station 206, or EMR server 214 (FIG. 13).

FIGS. 4 to 10 illustrate imaging information that is used as training data for the machine learning algorithm. As well, in FIGS. 4 to 10, the imaging information illustrates how the device 100 can be used in vivo to classify AD-associated pathologies in the eye of a particular subject (patient). Both scenario are described with reference to FIGS. 4 to 10.

FIG. 4 shows a Raman map 400 of unstained, formalin fixed, paraffin embedded (FFPE) brain tissue from postmortem AD patient. A bright spot corresponds to the location of an Amyloid Beta plaque, as independently verified through histology on an adjacent ex vivo tissue slice from the same subject. This map 400 is generated by the computer 6 by plotting the signal intensity at a wavenumber of 1663 cm−1 for every pixel (which corresponds to Raman vibrational resonances of Beta-sheet protein structures), and by subtracting a linear background of the Raman signal between 2000 cm−1 and 2500 cm−1. The axes correspond to physical units of distance (in units of micrometers) of the tissue slice. A bright spot 402 is at pixel (55 um, 46 um) of FIG. 4. In an example, a particular Raman capture can encompass more than one pixel of an ROI that is illuminated by the laser 18, for a single capture taken by the Raman unit spectroscopy unit. In another example, each pixel of the ROI is scanned by each pixel being stimulated by the monochromatic laser 18 and Raman spectroscopy information is acquired by Raman spectroscopy unit over each pixel of the ROI to create a Raman map of the ROI or to calculate integrated spectroscopy results over the ROI.

FIG. 5 shows a broadband Raman spectrum graph 500 of an AD plaque, corresponding to the bright spot 402 pixel (55 um, 46 um) of FIG. 4. The graph 500 illustrates counts of received Raman-scattered light versus wavenumber shift, for that pixel. Peaks 502, 504, at 1600 cm−1 and 1663 cm−1 correspond to Raman vibrational resonances of Alpha-helix and Beta-pleated sheet protein conformations, respectively; the so-called Amide I band. Most of the remaining peaks correspond to the presence of paraffin. The peaks at 1600 cm' and 1663 cm−1 indicate the presence of proteins in this location; these peaks are clearly visible against the low background signal present at these wavelengths in a neighboring region of the field of view (FIGS. 6, 602 and 604). This confirms the localized presence of the proteins that are characteristic of Amyloid Beta plaques. Noting that there is no Raman signal from beta sheets at 1800 cm−1, a map showing the ratio of Raman signal at 1663 cm−1 to 1800 cm−1, will show hot spots at locations corresponding to Amyloid Beta plaques. For a given level of background signal (noise'), a criteria may be set according to the ratio of signal at 1663 cm−1 to 1800 cm−1. For example, a signal-to-noise ratio of 3:1 may be used to identify the presence of Amyloid Beta plaques.

FIG. 6 shows a broadband Raman spectrum graph 600 of a background tissue pixel (10 μm, 15 um) of FIG. 4. Note the absence of peaks at 1600 cm−1 and 1663 cm−1, indicating the lack of Alpha-helix and Beta-pleated sheet protein conformations. This is independently verified through histology on an adjacent ex vivo tissue slice of the same subject. In some examples, the Raman spectrum graph 600 or other Raman spectroscopy information of background tissue can be used as control information (negative classification or as a value to be subtracted/divided out) for training of the machine learning algorithm.

In some examples, the Raman spectrum graph 600 obtained from the ROI of the present subject can be used by the machine learning algorithm to classify the plaque or AD-associated pathology. For example, the computer 6 performs a comparison between the Raman spectrum graph 600 for the background tissue of the subject and the Raman spectrum graph 500 (FIG. 5) for the potential plaque of the subject. The comparison provides useful results because the Raman spectrum graph 600 is taken from the same subject as for the Raman spectrum graph 500. The comparison can include machine learning algorithm, a comparison, a formula, a calculation, a table, a subtraction, a ratio, or other comparisons performed by the computer 6, in order to classify as the plaque or other AD-associated pathology.

In some examples, the Raman map of verified training data is generated by integrating the Raman signal over a spectral region and plotting this integrated quantity for every pixel. FIG. 7 shows such an example, wherein each pixel encodes the integrated counts between 1663 cm−1 and 1698 cm−1 for that area. A linear background signal based on the Raman spectrum between 2000 cm−1 and 2500 cm−1 has been subtracted as well. The bright spot 702 in FIG. 7 is easily identifiable and corresponds to an Amyloid Beta plaque, as independently confirmed through histology on an adjacent tissue slice.

In other examples, chemometrics may be used to infer the spectral regions that best correspond to AD-associated pathology. That is, an algorithmic, statistical analysis of the broad Raman spectrum may be performed to identify features specific to AD-associated pathology that are not readily apparent.

In some examples, rather than a single broad spectral range, the acquired Raman signal can comprise of one or more narrower spectral regions, or bands, centered on spectral regions of interest such as those identified in FIG. 5.

In an example, Raman spectroscopy is performed at one or more identified ROIs rather than performing a Raster scan over an extended area. The result in these cases will be a single Raman spectrum graph such as that shown in FIG. 5 rather than a full image comprising of Raman spectra at every pixel. In some cases, the incoming laser beam may be expanded to a larger diameter so as to cover a wider area and the Raman-scattered light will be collected from the ROI covered by the widened laser spot size.

FIG. 10 illustrates example hyperspectral imaging maps 1000 of the patient tissue, that illustrate hyperspectral imaging information that can be used for identifying one or more ROI for subsequent Raman spectroscopy. The hyperspectral imaging maps 1000 can include a plurality of individual hyperspectral image maps 1000a, 1000b, . . . , 1000e, each representing a map of counts of a specific detected wavelength from the hyperspectral camera 10. A higher (or lower) count at a pixel of a particular hyperspectral image map can mean that the pixel warrants further investigation using Raman spectroscopy. From the hyperspectral imaging maps 1000, the computer 6 can use the machine learning algorithm to determine one or more ROI 1002 (one shown), such as one or more pixels, that warrant further investigation by Raman spectroscopy. In other examples, each hyperspectral map 1000 can represent a range of wavelengths rather than one specific wavelength, with the count being for that particular range of wavelengths. In yet other examples, the hyperspectral map 1000 may be generated by using a particular linear combination of wavelengths, which best encapsulates the distinguishing features of AD-associated pathologies.

Another example representation of hyperspectral reflectance imaging information is a spectrum graph (not shown), for each pixel or region of the subject. The spectrum graph illustrates counts of received light versus wavelength, for that pixel. The hyperspectral imaging spectrum graph can also be used for training of the machine learning algorithm, and for classification performed by the machine learning algorithm.

In examples, the ROI can be determined from the hyperspectral imaging information, as illustrated in the hyperspectral imaging maps 1000 or the hyperspectral imaging spectrum graphs.

Referring still to FIG. 10, the computer 6 uses the machine learning algorithm to determine which of the hyperspectral reflectance maps 1000 and their corresponding wavelengths are to be processed, as some wavelengths of the hyperspectral imaging maps 1000 provide better results than others. For example, hyperspectral imaging maps 1000 corresponding to the entire visible and near-infrared spectrum do not need to be analyzed, but rather one or more specific wavelengths of the hyperspectral imaging maps 1000 are selected by the computer 6 for further processing. In some other examples, the hyperspectral imaging maps 1000 that are less relevant to the AD pathologies of interest are given less weight and the hyperspectral imaging maps 1000 that are more relevant are given more weight, for the computer 6 to determine the ROI for the Raman spectroscopy.

In one example, the hyperspectral imaging maps 1000 or the hyperspectral imaging spectrum graphs of interest that are used by the computer 6 are in the visible-near-infrared (VNIR) wavelength range (400 to 1400 nanometers), and can specifically be in the 460 nm to 600 nm optical wavelength range or in the 650 nm to 950 nm optical wavelength range, which can be more suitable for detecting protein aggregates such as Amyloid Beta deposits. Different or more specific wavelength ranges are used in other example embodiments, based on the particular AD-associated pathologies to be detected and the machine learning algorithm.

Referring again to FIG. 4, the hyperspectral reflectance maps 1000 (or the hyperspectral reflectance spectrum graphs) are generated and used by the computer 6 to determine a location and size of one or more specific ROIs of the subject to be further analyzed using Raman spectroscopy. The ROI can include one or more pixels. In this example the ROI is the bright spot at pixel (55 um, 46 um) of FIG. 4. Therefore, the entire field of view of the hyperspectral reflectance map does not need to be Raman scanned, but rather localized areas such as pixel (55 um, 46 um) of FIG. 4 have the Raman spectroscopy information detected by the Raman spectroscopy unit in a single capture, which is at the same location on the subject as ROI 1002 in FIG. 10. In some examples, a number of pixels surrounding the bright spot pixel, or a defined radius of pixels around the bright spot pixel, can also be analyzed with Raman spectroscopy in a single capture.

FIG. 7 shows another Raman map 700 of unstained, FFPE brain tissue from post-mortem AD patient. Once again, a bright spot corresponds to the location of an Amyloid Beta plaque, as independently verified through histology on an adjacent tissue slice of an ex vivo subject. The bright spot 702 is at pixel (17 um, 31 um) of FIG. 7. This map 700 was generated by plotting at every pixel the integrated Raman signal between 1663 cm−1 and 1698 cm−1, preceded by subtraction of a linear background of the Raman signal between 2000 cm−1 and 2500 cm−1. The axes correspond to physical units of distance (in units of micrometers) of the tissue slice.

FIG. 8 shows a broadband Raman spectrum graph 800 corresponding to the bright spot 702 pixel (17 urn, 31 urn) of FIG. 7. Peaks 802, 804 at 1600 clifl and 1663 cm−1 correspond to Raman vibrational resonances of the Amide I band, namely, Alpha-helix and Beta-pleated sheet conformations, respectively. Remaining peaks correspond to the presence of paraffin.

FIG. 9 shows a broadband Raman spectrum graph 900 of a background tissue pixel (45 urn, 10 um) in FIG. 7. Note the absence of peaks at 1600 cm−1 and 1663 cm−1, indicating the lack of Alpha-helix and Beta-pleated sheet protein conformations. This is independently verified through histology on an adjacent tissue slice (see FIG. 15). The Raman spectrum graph 900 or other Raman spectroscopy information of the background tissue pixels can be used as control (negative classification) information for training of the machine learning algorithm. The Raman spectrum graph 900 or other Raman spectroscopy information of the background tissue pixels can be used for a comparison or other calculation against the spectrum graph 800 (FIG. 8), for classifying of the plaque.

Referring again to FIG. 7, one or more of the hyperspectral reflectance maps 1000 (FIG. 10) can be used by the computer 6 to determine a location and size of a specific ROI of the eye of the subject to be further investigated using Raman spectroscopy. In this example the ROI is the bright spot at pixel (17 um, 21 um) of FIG. 7. Therefore, the entire field of view of the Raman map 700 in FIG. 7 does not need to be Raman scanned when assessing for AD pathology. Rather, localized areas such as pixel (17 urn, 21 urn) of FIG. 7 are detected by Raman spectroscopy at the same location on the subject as ROI 1002 in FIG. 10. In one example, Raman spectroscopy of the ROI is detected in a single capture by the Raman spectroscopy unit. In another example, the ROI is scanned pixel-by-pixel, to generate a Raman map of the ROI or to calculate integrated counts of specified wavelength(s) of interest.

The results in FIGS. 4 to 10 illustrate verified training data that can be used for training of the classification and detection of Amyloid Beta plaque in the subject. In other example embodiments, other AD-associated pathologies are classified instead of, or in addition to, the Amyloid Beta plaques. For example, when the AD-associated pathology is Tau neurofibrillary tangles, the Raman resonance wavelength of interest remains the same (1600 cm−1-1700 cm−1 for phosphorylated-Taus) but now are found inside the cells.

For other AD-associated pathologies, yet other Raman resonance wavelengths may be used to classify and detect the AD-associated pathologies.

FIG. 13 illustrates a system 200 for detecting AD pathologies in the eye of a subject, in accordance with an example embodiment. In some examples, the system 200 implements the machine learning algorithm in order to operate the device 100 on the subject. The system 200 includes the device 100, a server 204, a client station 206, and an electronic medical record (EMR) server 214. There can be more than one of each type of device in the system 200. The devices of the system 200 can communicate over a network 202. The client station 206 can be a computer, a laptop, a mobile phone, a tablet computer, etc. The network 202 can include Local Area Networks (LANs), wireless wide area networks (WWANs), private networks, and the Internet. The computer 6 (FIG. 1) of the device 100 has a communication subsystem for communicating over the network 202.

In FIG. 13, the server 204 is typically remote to the device 100 and is configured to train the machine learning algorithm. The server 204 can include one or more dedicated servers, or one or more cloud servers. In some examples, the server 204 can include or can access a third-party machine learning platform such as Amazon™ AWS, Microsoft™ Azure, Google™ Cloud and IBM™ Watson. The server 204 can include a machine learning module 218 and a memory 216 for storing a database of the verified training data and for storing trained neural networks. The server 204 can include one or more controllers or processors (not shown) that are configured to execute instructions stored in the memory 216.

The EMR server 214 can be used to store, deposit, and retrieve electronic medical records of patients. The EMR server 214 can include a memory that is a data repository for patient data. The EMR server 214 can be a third party server in an example. The EMR server 214 can contain medical, demographic, and physical information of patients. The EMR server 214 can contain verified training data in some examples.

The memory 216 or the EMR server 214 can contain previous hyperspectral imaging information or Raman spectroscopy information of a particular patient, so that they can be compared with other Raman spectroscopy information of the patient taken at other times so that the computer 6 or server 204 can perform AD conclusions for the particular patient. For example, time-separated hyperspectral imaging information or Raman spectroscopy information of the same patient at the same ROI can be compared to personal history of the same patient to see a progression (regression). The progression (regression) of the patient can also be compared to other population cohorts and their historical progression (regression).

The server 204 can implement the machine learning algorithm by way of one or more neural networks. The machine learning algorithm can include logistic regression, variational autoencoding, convolutional neural networks, or other statistical techniques used to identify and discern AD-associated pathologies. The machine learning algorithm can also use Raman scattering models, other scattering models, or optical physics models that are validated a priori. The neural network may comprise a plurality of layers, some of which are defined and some of which are undefined (or hidden). The neural network is a supervised learning neural network.

In some examples, the neural network may include a neural network input layer, one or more neural network middle hidden layers, and a neural network output layer.

Each of the neural network layers include a plurality of nodes (or neurons). The nodes of the neural network layers are connected, typically in series. The output of each node in a given neural network layer is connected to the input of one or more nodes in a subsequent neural network layer. Each node is a logical programming unit that performs an activation function (also known as a transfer function) for transforming or manipulating data based on its inputs, a weight (if any) and bias factor(s) (if any) to generate an output. The activation function of each node results in a particular output in response to particular input(s), weight(s) and bias factor(s). The inputs of each node may be scalar, vectors, matrices, objects, data structures and/or other items or references thereto. Each node may store its respective activation function, weight (if any) and bias factors (if any) independent of other nodes. In some example embodiments, the decision of one or more output nodes of the neural network output layer can be calculated or determined using a scoring function and/or decision tree function, using the previously determined weight and bias factors, as is understood in the art.

The server 204 can train the neural network using verified training data 208 as input by a practitioner into the client station 206. Additional training datasets can be obtained from the EMR server 214 or from operation of the device 100 itself. For example, operation of the device 100 results in acquisition of hyperspectral reflectance information and Raman spectroscopy information, which is stored in the server 204 or in the EMR server 214. Additional subsequent Raman captures can be performed at a later time to obtain more Raman spectroscopy information. The historical trend of the hyperspectral reflectance information and Raman spectroscopy information may be verified at a later date as being indicative of AD or as a precursor to AD. For example, many years or decades later, the subject may be diagnosed as having AD, and this diagnosis can be classified with earlier hyperspectral reflectance information and Raman spectroscopy information as being AD or pre-AD. Similarly, some subjects may have their EMR information updated in subsequent years, and may be indicated as not having AD. In some examples, post mortem histology can be used to verify the AD information of the patient. The histology can be performed using a microscope or other imaging modalities.

In some examples, the server 204 can implement two neural networks. As understood in the art, each neural network can themselves have one or more neural networks, in parallel, series, or other arrangements. The first neural network is used to identify the one or more ROI as the output of the first neural network based on hyperspectral reflectance information as the input to the first neural network. The second neural network is used to classify the Raman spectra returned from interrogation of these particular ROI, with Raman spectroscopy information as the input to the second neural network. The output of the second neural network is a classification of whether each of the ROI contain or do not contain the one or more AD-related pathologies of interest, such as protein aggregates.

In some examples, the classification (output of the second neural network) can be one or more AD conclusion as to whether the subject has AD, or a precursor to AD, or is pre-screened for potential AD and requires further investigation. Such AD conclusions can be based on one or a plurality of AD pathologies that are classified by the second neural network, and determined or calculated using e.g. a combined weighted score, scorecard, or probabilistic determination. For example, the presence or probabilistic classification of both Amyloid Beta and Tau neurofibrillary tangles may lead to a higher probability conclusion of AD. In some examples, the AD conclusions can also be based on the changes over time of the patient physiology, for example by comparing with previous Raman spectroscopy information of the patient. In some examples, the hyperspectral reflectance information is also used as input information to the second neural network, which further assists in classifying AD pathologies.

Training of the neural networks using the server 204 will now be described in greater detail. Verified training data 208 is input to the client station 206, and is then transmitted by the client station 206 to the server 204. In example embodiments, the verified training data 208 is obtained by comparing adjacent ex vivo tissue slices of a subject, with one slice being analyzed to obtain hyperspectral reflectance information and Raman spectroscopy information, and the adjacent slice verified through histology, resulting in verified hyperspectral reflectance information and verified Raman spectroscopy information. For training of the first neural network, the verified hyperspectral reflectance information 210 is input to the client station 206. In an example, the verified hyperspectral reflectance information 210 correlates counts of a specific wavelength of a hyperspectral reflectance map to one or more AD-associated pathologies. For training of the second neural network, verified Raman spectroscopy information 212 is input to the client station 206. In one example, the verified Raman spectroscopy information 212 correlates counts of a specific wavelength of a ROI or a Raman map to one or more AD-associated pathologies.

In some examples, the hyperspectral reflectance information can be used for more than training of the first neural network to determine the ROI. For example, the hyperspectral reflectance information can also be used for training of the second neural network, to assist in classifying the particular AD-associated pathology. The hyperspectral reflectance information can be used together with the Raman spectroscopy information, and given weight or further assurance when classifying the particular AD-associated pathology. As well, the machine learning algorithm may determine correlations and relationships between the hyperspectral information and the Raman spectroscopy information, for classifying of the particular AD-associated pathology. When the computer 6 executes the trained neural network and uses both the hyperspectral reflectance information and the Raman spectroscopy information for the classifying, co-registration can be digitally performed by the computer 6 on the hyperspectral reflectance information and the Raman spectroscopy information in order to align the same ROI.

In some examples, a ROI can include a group of pixels covering the plaque. In one example, the size (e.g., circular area indicated by radius or rectangular area indicated by M×N pixels) of the plaque is used to classify the AD-associated pathology. In some examples, the Raman spectroscopy information 212 may have higher counts for a specific wavelength at the center of the ROI, and less counts at the periphery of the ROI (but still higher than background tissue). In some examples, the individual counts at the different pixels within a ROI can be used for classifying of the AD-associated pathology. In other examples, the aggregate (integrated) characteristics of the group of pixels in the ROI may be used to classify the plaque, for example in one Raman capture. Therefore, the size of the ROI of the plaque can also be part of the training of the second neural network, to be used as additional information in order to classify the plaque.

In some examples, Raman spectroscopy information 212 of the background tissue of the subject is also included in the verified training data 208. The Raman spectroscopy information of the background tissue of a given patient can be used to compare with the Raman spectroscopy information of ROI of that patient. The comparison between the background tissue and the ROI can be part of the training of the second neural network to classify the AD-associated pathology. Other algorithms or calculations, including logistic regression, variational auto-encoding, convolutional neural networks, and other statistical approaches, can be used for the supervised training of the second neural network.

Once the server 204 has trained the neural networks, the server 204 can transmit the trained neural networks to the device 100 for execution of the trained neural networks by the computer 6. The computer 6 is now informed of the criteria that should be used to assess the AD-associated pathologies of interest. Training updates to the neural networks can be performed by the server 204 periodically, in real-time, or whenever there is more available training data, and those updated neural networks can be sent to the device 100.

In other examples, at least some or all of the neural networks are executed by the server 204, and detected hyperspectral reflectance information, detected Raman spectroscopy information, and control information are communicated between the server 204 and the computer 6. In such an example, the server 204 executes the neural networks by receiving hyperspectral reflectance information from the computer 6 and instructing the computer 6 as to what are the ROI for the Raman spectroscopy unit. The server 204 receives the Raman spectroscopy information from the computer 6 and classifies the AD-associated pathologies or AD conclusions.

FIG. 11 illustrates a flow diagram of a method 1100 implemented by the device 100 for detecting AD-associated pathologies in the eye of a subject, in accordance with an example embodiment. The computer 6 of the device 100 uses the neural networks for at least some of the method 1100, in an example embodiment. At step 1102, the device 100 performs wide field-of-view imaging of the fundus of the subject, by controlling the hyperspectral reflectance imaging unit (FIG. 1) and receiving hyperspectral reflectance information from the hyperspectral reflectance imaging unit. At step 1104, using hyperspectral reflectance information from the hyperspectral reflectance imaging unit and the first neural network, the computer 6 determines a location and size of one or more ROI of the subject that warrants further inspection. At step 1106, the device 100 performs Raman spectroscopy on the ROI by controlling the Raman spectroscopy unit (FIG. 1) to stimulate the ROI at the determined location and size in a single capture, and receiving Raman spectroscopy information from the Raman spectroscopy unit. At step 1108, the second neural network uses the Raman spectroscopy information obtained from the Raman spectroscopy unit for the ROI, as well as hyperspectral reflectance information from the hyperspectral reflectance imaging unit, to classify one or more AD-associated pathologies or AD conclusions. At step 1110, the device 100 outputs the classification(s) to an output device (e.g. display screen), a memory, or another computer. In some other examples, steps 1108 and 1110 is performed by the server 204. In example embodiments, when multiple AD-associated pathologies of interest are to be detected, the method 1100 can be performed for all of the AD-associated pathologies (parallel determination) on one or more ROI to detect all of the AD-associated pathologies of interest. When there is a positive diagnosis by a practitioner, histologist, pathologist, etc., of the same sample, the client station 206 can be used by such a practitioner to positively (and independently) verify that the subject has one or more AD-associated pathologies or AD. Such verification can be used by the machine learning algorithm (first and second neural networks) as further training data, in order to improve the machine learning algorithm.

In some examples, after step 1106, the device 100 can be configured to have looping 1112 back to step 1102 in order to determine Raman spectroscopy of another ROI that was identified by the hyperspectral reflectance imaging unit that may require further investigation by the Raman spectroscopy unit. The looping 1112 can be performed in the same session, e.g., within the sequential time while the user is still resting on the chin rest 5. For example, at step 1104, the computer 6 may have determined more than one ROI of the subject that may warrant further inspection, and therefore the looping 1112 is performed to investigate those other ROIs. The classifying at step 1108 can provide a conclusion based on a plurality of different individual captures of the same subject, taken by the hyperspectral reflectance imaging unit and the Raman spectroscopy unit. In other examples, the looping 1112 is not performed and only one Raman capture is performed on one ROI, having a specific position and size as determined from the hyperspectral reflectance imaging information.

In some examples, using the hyperspectral reflectance information from the hyperspectral reflectance imaging unit, the computer 6 determines a baseline ROI in relation to a part of the eye that is not a potential AD-associated pathology (using the machine learning algorithm or a default position). The baseline ROI can be analyzed using Raman spectroscopy. At step 1108, the computer 6 can compare the baseline ROI with one or more of the ROI that are analyzed using Raman spectroscopy, for classifying the one or more AD-associated pathologies or AD conclusions.

In some examples, at step 1104, the computer 6 has pre-saved one or more potential AD-associated pathologies of interest (or specific ROI) in relation to that particular patient (or verified from known patient populations). For example, a previous session using the device 100 had pre-saved one or more one or more potential AD-associated pathologies. Particular landmarks can be used to locate the one or more potential AD-associated pathologies in the particular patient, such as an arterial vessel, the optic nerve, etc. Using hyperspectral reflectance information from the hyperspectral reflectance imaging unit and the first neural network, the computer 6 locates those pre-saved potential AD-associated pathologies (or specific ROI) of the patient, determines an appropriate ROI, and then the computer 6 further investigates the appropriate ROI using the Raman spectroscopy unit, all during the same session while the user is still resting on the chin rest 5.

FIG. 12 illustrates a flow diagram of a method 1200 for determining the verified training data 208 for the neural networks, in accordance with an example embodiment. Generally, the verified training data 208 can be obtained by comparing adjacent ex vivo tissue slices from a subject, with one slice being analyzed by the hyperspectral reflectance imaging unit and the Raman spectroscopy unit, and the adjacent slice verified through histology. An example result of the method 1200 is the Raman spectroscopy information 212 illustrated in FIGS. 4 to 9, and the hyperspectral reflectance information 210 illustrated in the hyperspectral maps 1000 shown in FIG. 10. Additionally, in some examples, in vivo imaging from operation of the device 100 may also be used to obtain further training data.

In the method 1200, ex vivo human brain tissue (cortex) from a deceased, confirmed AD patient was obtained. Both fresh frozen as well as formalin fixed, paraffin embedded (FFPE) were used as the sample. At step 1202, the sample is sliced and placed on slides. Microtome or cryostat were used to cut 12 um thick slices of the sample. A series of adjacent such slices were cut and placed on microscope slides. At step 1204, every second slice in the series is stained with Congo red, which binds to Amyloid Beta, or similar staining procedure, such as immunostaining, for example. The remaining intervening slides are left unstained. At step 1206, using standard polarization microscopy or other histology methods, Amyloid Beta plaques are identified on the stained slides. The histology can be performed manually by a clinician, automatically by a computer, or both. The typical size of brain plaques are greater than 20 um in diameter; therefore, a given plaque has a high likelihood of spanning across multiple 12 um slices.

At step 1208, the stained slides having one or more plaques are each co-registered with their adjacent unstained slide. Co-registration can be done automatically using a computer, performed manually, or both. Co-registration of adjacent slides allows for identification of the location of the plaque on the unstained slide. Co-registration is achieved by looking at multiple features of various size scales. Folds in the cortex provide large scale features used for general orientation of two adjacent slices. Blood vessels constitute smaller features used to co-register adjacent slices on a finer size scale. Using multiple vessels within an image, and co-locating these in adjacent slices facilitates location of a given plaque to within a few micrometers. By overlaying images of two adjacent slices, alignment of blood vessels allows for co-registration of images in one example.

At step 1210, at the corresponding location of the stained slide, an imaging modality is performed on the co-registered location of the adjacent unstained slide to determine the imaging characteristics of the AD-associated pathology. In other examples, the entire adjacent unstained slide is imaged using the imaging modality, e.g. to obtain additional information on background tissue, other AD-associated pathologies, macro structures, etc. In example embodiments, the imaging modality can be hyperspectral reflectance imaging or Raman spectroscopy, as described in detail herein. At step 1212, after the imaging information for the plaque is acquired, the imaging information (or processed imaging information) is classified as the plaque. The verified hyperspectral reflectance information 210 is correlated with the Amyloid Beta plaques in this example. An example of the verified hyperspectral reflectance information 210 is the hyperspectral image shown in FIG. 16. The verified Raman spectroscopy information 212 is also correlated with Amyloid Beta plaques in this example, see FIG. 7. An example of the Raman spectroscopy information 212 is the Raman spectroscopy information 500, 800 shown in FIGS. 4 and 8, respectively.

The verified training data 208 is input to the client station 206, and can be transmitted to the server 204 for training of the neural networks.

The method 1200 can be repeated for other AD-associated pathologies such as Taupathy, other protein aggregates, and vascular characteristics, in order to obtain further verified training data 208. Any non-plaque regions of background tissue that are detected using the image modality can be used as control information or negative-classification information, for training of the neural networks. The background tissue can also be used for a subtraction or division calculation from a count of the ROI in order to classify the ROI as being a plaque. Other non-plaque regions can have macrostructures for co-registration, e.g. for relative location information of parts of interest within the subject. The detection of the background tissue can also be used for training of the neural networks.

The method 1200 can be repeated for multiple tissue samples from one subject, e.g. both brain tissue and eye tissue from one subject. The method 1200 can be repeated for tissue samples from different subjects. By using multiple tissue samples, a sufficient sample set is used for determining the verified training data 208 for the machine learning algorithm. Baseline or control training data can also obtained by obtaining hyperspectral reflectance information 210 and Raman spectroscopy information 212 and from healthy (non-AD) subjects.

FIG. 14 illustrates a polarization microscopy image 1400 that includes a plaque 1402 (e.g. a stained red spot), corresponding to the Raman map 400 of FIG. 4. The polarization microscopy image 1400 can be used to verify that the Raman map 700 includes Raman spectroscopy information that contains the plaque 1402, at the same ROI.

FIG. 15 illustrates two different magnifications (10×, left and 40×, right) of polarization microscopy images of a stained slide, showing plaque 1502, 1504 (e.g. the stained red spot) next to a vessel, corresponding to the Raman map 700 of FIG. 7 (mirror image). The polarization microscopy images can be used to verify that the Raman map 700 includes Raman spectroscopy information that contains the plaque 1502, 1504, at the same ROI.

FIG. 16 illustrates a hyperspectral image 1600 of an unstained slide (left), containing the same vessel 1602 as seen in FIG. 15 in an adjacent slice, and a polarization microscopy image of same (right), showing the same vessel 1604 in the same adjacent slice.

The Raman spectroscopy unit 1 can also be configured to take white light images. FIG. 17A illustrates a white light image 1700 of the same unstained slide (the same adjacent slice) as shown in FIG. 16, taken by the Raman spectroscopy unit. FIG. 17A which shows that the same vessel 1702 as shown in FIG. 16 can be located and captured by the device 100 using the Raman spectroscopy unit.

FIG. 17B illustrates the white light image 1700 of FIG. 17A, showing a region 1704 of the vessel 1702 that has been captured using Raman spectroscopy. The region 1704 can have a specific position and size as determined by the hyperspectral image 1600, and can be taken in a single capture by the Raman spectroscopy unit. In other examples, the region 1704 can be scanned pixel-by-pixel using the Raman spectroscopy unit, in order to generate a map or calculate integrated counts of specific wavelengths.

Referring again to FIG. 1, in some examples, the device 100 can implement other types of imaging modalities to determine a specific wavelength or wavelengths that are characteristic of the chemical constituents of the potential AD pathologies in the ROI. In an example, the imaging modality is implemented using Inverse Raman Effect with one source being a broadband light source and the second source being a coherent single wavelength source at specific wavelengths.

In another example, the imaging modality is implemented using Stimulated Raman Effect with two coherent lasers at specific wavelengths. In another example, the imaging modality is implemented by using auto-fluorescence measurements at several different wavelengths using pulse light coherent illumination sources.

In some examples, another imaging modality such as a white light non-hyperspectral fundus camera can be used. This additional imaging modality can be used to guide a positioning of the wide field-of-view of the hyperspectral reflectance imaging unit. Such positioning can be performed automatically by the computer 6 using image information from this additional imaging modality, and/or can be performed manually by the operating clinician. The computer 6 can use machine learning and one or more neural networks to automatically perform the positioning.

In example embodiments, some of the components of the system 200 are mounted, tightened and enclosed in order to reduce relative movements, vibrations and reduce amount of foreign electromagnetic radiation entering the system 200.

In example embodiments, the computer 6, the server 204, and any of the devices of the system 200 can include one or more communication subsystems (wired or wireless) and one or more controllers. The controllers can comprise hardware, software, or a combination of hardware and software, depending on the particular application, component or function. In some example embodiments, the one or more controllers can include analog or digital components, and can include one or more processors, one or more non-transitory storage mediums such as memory storing instructions executable by the one or more processors, and/or one or more analog circuit components.

An example embodiment is a non-invasive in vivo ocular light-based detection device for detection of one or more AD-associated pathologies from an eye of a subject, comprising: a hyperspectral reflectance imaging unit that includes a broadband light source and a hyperspectral camera; a Raman spectroscopy unit that includes a laser and a spectrometer; memory; and one or more processors configured to execute instructions stored in the memory to: control the hyperspectral reflectance imaging unit to illuminate a wide field-of-view of a fundus of the eye using the broadband light source, and detect resulting reflected and/or backscattered light from the eye using the hyperspectral camera for determining hyperspectral reflectance information, determine one or more ROI from the hyperspectral reflectance information as being a potential AD-associated pathology, control the Raman spectroscopy unit to illuminate each of the one or more ROI using the laser, and detect Raman scattered light from the eye resulting from the laser and using the spectrometer for determining Raman spectroscopy information, and classify, using the hyperspectral reflectance information and the Raman spectroscopy information, the subject as having one or more AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

In any of the above example embodiments, the classifying of the subject as having the one or more AD-associated pathologies is further based on the hyperspectral reflectance information.

In any of the above example embodiments, the classifying of the subject as having the one or more AD-associated pathologies is further based on previous hyperspectral reflectance information and/or Raman spectroscopy information of the subject stored in the memory or in another device.

In any of the above example embodiments, the classifying of the subject as having the one or more AD-associated pathologies is further based on changes in the hyperspectral reflectance information and/or the Raman spectroscopy information of the subject over time.

In any of the above example embodiments, the classifying of the subject as having the one or more AD-associated pathologies comprises classifying the subject as having a plurality of the AD-associated pathologies.

In any of the above example embodiments, the one or more processors are further configured to: determine a baseline ROI from the hyperspectral imaging information as being background tissue that does not contain the potential AD-associated pathology, and control the Raman spectroscopy imaging unit to illuminate the baseline ROI of the eye using the laser, and detect light from the eye resulting from the laser using the spectrometer for determining Raman spectroscopy information of the background tissue, wherein the classifying is further based on comparing the Raman spectroscopy information of the potential AD-associated pathology with the Raman spectroscopy information of the background tissue.

In any of the above example embodiments, the one or more AD-associated pathologies include two or more of the AD-associated pathologies including the Tau neurofibrillary tangles.

In any of the above example embodiments, the one or more AD-associated pathologies include neuritic or glial cytopathology of the eye of the subject, or vascular characteristics of blood vessels or choroid of the eye of the subject.

In any of the above example embodiments, when the one or more AD-associated pathologies include the Amyloid Beta deposits, the classifying is based on analyzing Raman spectroscopy information at a wavenumber shift or shifts in a range of 1600 cm−1 to 1700 cm−1, which correspond to Raman vibrational resonances of Alpha-helix and Beta-pleated sheets.

In any of the above example embodiments, when the one or more AD-associated pathologies include the Tau neurofibrillary tangles, wherein the classifying is based on analyzing Raman spectroscopy information at a wavenumber shift or shifts in a range of 1600 cm−1 to 1700 cm−1, which corresponds to Raman vibrational resonance of phosphorylated-Taus.

In any of the above example embodiments, the one or more processors use a machine learning algorithm for one or both of: the determining of the one or more ROI; or the classifying of the subject as having one or more AD-associated pathologies.

In any of the above example embodiments, the machine learning algorithm uses verified training data In any of the above example embodiments, the verified training data is obtained by: slicing an ex vivo tissue sample from a subject into tissue slices; placing the tissue slices onto slides; staining a first slide of one of the tissue slices; providing a second slide having another tissue slice that was adjacent to the first tissue slice in the tissue sample and is unstained; verifying that the first slide has one or more of the AD-associated pathologies using histology; performing at least one imaging modality on the second slide to obtain imaging information; and classifying the imaging information as one or more of the AD-associated pathologies.

In any of the above example embodiments, the at least one imaging modality is the Raman spectroscopy unit, the hyperspectral reflectance imaging unit, or both.

In any of the above example embodiments, the machine learning algorithm uses one or more neural networks.

In any of the above example embodiments, the one or more processors are further configured to: further train the machine learning algorithm using: i) the classifying of the one or more AD-associated pathologies, and ii) independent verification of the subject as having the one or more AD-associated pathologies.

In any of the above example embodiments, the one or more processors are further configured to classify, from the Raman spectroscopy information, the subject as having: AD, or a precursor to AD, or a pre-screened classification for potential AD that requires further investigation, or responsiveness to treatment or intervention.

In any of the above example embodiments, exogenous fluorescing agents, dyes, or tracers are not required for the classifying of the one or more AD-associated pathologies.

In any of the above example embodiments, the device further comprises one or more optical filters to filter out a wavelength of the laser prior to detection by the spectrometer.

In any of the above example embodiments, the one or more processors are configured to determine a respective size of each of the one or more ROI from the hyperspectral reflectance information, and control of the Raman spectroscopy unit to emit the laser onto each of the ROI of the eye having the respective size.

In any of the above example embodiments, the Raman spectroscopy unit is controlled by the one or more processors to perform, for each of the one or more ROI, scanning of the respective ROI using the laser of the Raman spectroscopy unit for the determining of the Raman spectroscopy information.

In any of the above example embodiments, wherein the hyperspectral camera includes: a 2-dimensional array of light sensors, each light sensor sensitive to a range of wavelengths of light; and a 2-dimensional filter array that overlays the array of light sensors, each individual filter selectively transmits light of a specific wavelength.

Another example embodiment is a method of non-invasive in vivo detection of one or more AD-associated pathologies from an eye of a subject, comprising: controlling a hyperspectral reflectance imaging unit to illuminate a wide field-of-view of a fundus of the eye using a broadband light source; detecting light from the eye resulting from the broadband light source using a hyperspectral camera for determining hyperspectral reflectance information; determining, using one or more processors, a location of one or more ROI from the hyperspectral reflectance information as being a potential AD-associated pathology; controlling a Raman spectroscopy unit to illuminate each of the one or more ROI using a laser; detecting Raman scattered light from the eye resulting from the laser using a spectrometer for determining Raman spectroscopy information; and classifying, using the one or more processors, using the hyperspectral reflectance information and the Raman spectroscopy information, the subject as having one or more AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

Another example embodiment is a computer program product by a machine learning training process, the computer program product comprising instructions stored in a non-transitory computer readable medium which, when executed by a computer, causes the computer to carry out non-invasive in vivo detection of one or more Alzheimer's Disease (AD)-associated pathologies from an eye of a subject, the machine learning training process comprising: training, using one or more processors, the computer program using verified training data, the verified training data obtained by: slicing an ex vivo tissue sample from a subject into tissue slices, placing the tissue slices onto slides, staining a first tissue slice of a first slide, providing a second slide having a second tissue slice that was adjacent to the first tissue slice in the tissue sample and is unstained, verifying that the stained first tissue slice has one or more of the AD-associated pathologies using histology, performing at least one imaging modality on the second slide to obtain imaging information, and classifying the imaging information as one or more of the AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein.

In any of the above example embodiments, the verified training data is further obtained by co-registering the first tissue slice with the second tissue slice.

In any of the above example embodiments, the at least one imaging modality is a Raman spectroscopy unit, a hyperspectral reflectance imaging unit, or both the Raman spectroscopy unit and the hyperspectral reflectance imaging unit.

In any of the above example embodiments, the performing at least one imaging modality comprises performing at least two imaging modalities which are collectively used for the classifying the imaging information as one or more of the AD-associated pathologies.

Another example embodiment is a method for machine learning training of a computer program stored in a memory which, when executed by a computer, causes the computer to carry out non-invasive in vivo detection of one or more AD-associated pathologies from an eye of a subject, the method comprising: training, using one or more processors, the computer program using verified training data, the verified training data obtained by: slicing an ex vivo tissue sample from a subject into tissue slices, placing the tissue slices onto slides, staining a first tissue slice of a first slide, providing a second slide having a second tissue slice that was adjacent to the first tissue slice in the tissue sample and is unstained, verifying that the stained first tissue slice has one or more of the AD-associated pathologies using histology, performing at least one imaging modality on the second slide to obtain detection information, and classifying the detection information as one or more of the AD-associated pathologies, the one or more AD-associated pathologies including protein aggregates, the protein aggregates including at least one of: Tau neurofibrillary tangles, Amyloid Beta deposits, soluble Amyloid Beta aggregates, or Amyloid precursor protein; and storing the trained computer program to the memory.

While some of the present embodiments are described in terms of methods, a person of ordinary skill in the art will understand that present embodiments are also directed to various apparatus such as processors, circuitry, and controllers including components for performing at least some of the aspects and features of the described methods, be it by way of hardware components, software or any combination of the two, or in any other manner, as applicable.

In the Figures, as applicable, at least some or all of the illustrated subsystems or blocks may include or be controlled by a processor, which executes instructions stored in a memory or non-transitory computer readable medium. Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the example embodiments, such variations being within the intended scope of the present disclosure. In particular, features from one or more of the above-described embodiments may be selected to create alternative embodiments comprised of a sub-combination of features, which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

What is claimed is:

1. A non-invasive in vivo ocular light-based detection system for detection of one or more Alzheimer's Disease (AD)-associated pathologies from an eye of a subject, comprising:

a hyperspectral reflectance imaging unit that includes a broadband light source and a hyperspectral camera;

a Raman spectroscopy unit that includes a laser and a spectrometer;

a memory; and one or more processors configured to execute instructions stored in the memory to:

control the hyperspectral reflectance imaging unit to illuminate a wide field-of-view of a fundus of the eye using the broadband light source, and detect resulting reflected and/or backscattered light from the eye using the hyperspectral camera for determining hyperspectral reflectance information;

determine one or more region of interest (ROI) from the hyperspectral reflectance information as being a potential AD-associated pathology;

control the Raman spectroscopy unit to illuminate each of the one or more ROI using the laser, and detect Raman scattered light from the eye resulting from the laser and using the spectrometer for determining Raman spectroscopy information; and classify, using the hyperspectral reflectance information and the Raman spectroscopy information, the subject as having one or more AD-associated pathologies, the one or more AD-associated pathologies including protein aggregates, the protein aggregates including at least one of Tau neurofibrillary tangles, Amyloid Beta deposits, soluble Amyloid Beta aggregates, or Amyloid precursor protein.

2. The detection system of claim 1, wherein the classifying of the subject as having the one or more AD-associated pathologies is further based on previous hyperspectral reflectance information and/or Raman spectroscopy information of the subject stored in the memory or in another device.

3. The detection system of claim 1, wherein the classifying of the subject as having the one or more AD-associated pathologies is further based on changes in the hyperspectral reflectance information and/or the Raman spectroscopy information of the subject over time.

4. The detection system of claim 1, wherein the classifying of the subject as having the one or more AD-associated pathologies comprises classifying the subject as having a plurality of the AD-associated pathologies.

5. The detection system of claim 1, wherein the one or more processors are further configured to:

determine a baseline ROI from the hyperspectral reflectance information as being background tissue that does not contain the potential AD-associated pathology; and control the Raman spectroscopy unit to illuminate the baseline ROI of the eye using the laser, and detect light from the eye resulting from the laser using the spectrometer for determining Raman spectroscopy information of the background tissue, wherein the classifying is further based on comparing the Raman spectroscopy information of the potential AD-associated pathology with the Raman spectroscopy information of the background tissue.

6. The detection system of claim 1, wherein the one or more AD-associated pathologies include two or more AD-associated pathologies including the Tau neurofibrillary tangles.

7. The detection system of claim 1, wherein the one or more AD-associated pathologies include neuritic or glial cytopathology of the eye of the subject, or vascular characteristics of blood vessels or choroid of the eye of the subject.

8. The detection system of claim 1, wherein when the one or more AD-associated pathologies include the Amyloid Beta deposits, the classifying is based on analyzing Raman spectroscopy information at a wavenumber shift or shifts in a range of 1600 $cm^{-1}$ to 1700 $cm^{-1}$, which corresponds to Raman vibrational resonances of Alpha-helix and Beta-pleated sheets.

9. The detection system of claim 1, wherein when the one or more AD-associated pathologies include the Tau neurofibrillary tangles, the classifying is based on analyzing Raman spectroscopy information at a wavenumber shift or shifts in a range of 1600 $cm^{-1}$ to 1700 $cm^{-1}$, which corresponds to Raman vibrational resonance of phosphorylated-Taus.

10. The detection system of claim 1, wherein the one or more processors use a machine learning algorithm for one or both of:

the determining of the one or more ROI; or the classifying of the subject as having one or more AD-associated pathologies.

11. The detection system of claim 10, wherein the machine learning algorithm uses verified training data.

12. The detection system of claim 11, wherein the verified training data is obtained by:

slicing an ex vivo tissue sample from a subject into tissue slices;

placing the tissue slices onto slides;

staining a first slide of a first tissue slice;

providing a second slide having another tissue slice that was adjacent to the first tissue slice in the tissue sample and is unstained;

verifying that the first slide has one or more of the AD-associated pathologies using histology;

performing at least one imaging modality on the second slide to obtain imaging information; and classifying the imaging information as being indicative of one or more of the AD-associated pathologies.

13. The detection system of claim 12, wherein the at least one imaging modality is the Raman spectroscopy unit, the hyperspectral reflectance imaging unit, or both.

14. The detection system of claim 10, wherein the machine learning algorithm uses one or more neural networks.

15. The detection system of claim 10, wherein the one or more processors are further configured to train the machine learning algorithm using:

the classifying of the subject as having the one or more AD-associated pathologies; and independent verification of the subject as having the one or more AD-associated pathologies.

16. The detection system of claim 1, wherein the one or more processors are further configured to classify, from the Raman spectroscopy information, the subject as having AD, a precursor to AD, a pre-screened classification for potential AD that requires further investigation, or responsiveness to treatment or intervention.

17. The detection system of claim 1, wherein exogenous fluorescing agents, dyes, or tracers are not required for the classifying of the one or more AD-associated pathologies.

18. The detection system of claim 1, further comprising one or more optical filters to filter out a wavelength of the laser prior to detection by the spectrometer.

19. The detection system of claim 1, wherein the one or more processors are further configured to:

determine a respective size of each of the one or more ROI from the hyperspectral reflectance information; and control the Raman spectroscopy unit to emit the laser onto each of the one or more ROI of the eye having the respective size.

20. The detection system of claim 1, wherein the Raman spectroscopy unit is controlled by the one or more processors to perform, for each of the one or more ROI, scanning of a respective ROI using the laser of the Raman spectroscopy unit for the determining of the Raman spectroscopy information.

21. The detection system of claim 1, wherein the hyperspectral camera includes:

a 2-dimensional array of light sensors, each light sensor sensitive to a range of wavelengths of light; and a 2-dimensional filter array that overlays the array of light sensors, wherein each individual filter selectively transmits light of a specific wavelength.

22. A method of non-invasive in vivo detection of one or more Alzheimer's Disease (AD)-associated pathologies from an eye of a subject, comprising:

controlling a hyperspectral reflectance imaging unit to illuminate a wide field-of-view of a fundus of the eye using a broadband light source;

detecting light from the eye resulting from the broadband light source using a hyperspectral camera for determining hyperspectral reflectance information;

determining, using one or more processors, a location of one or more region of interest (ROI) from the hyperspectral reflectance information as being a potential AD-associated pathology;

controlling a Raman spectroscopy unit to illuminate each of the one or more ROI using a laser;

detecting Raman scattered light from the eye resulting from the laser using a spectrometer for determining Raman spectroscopy information; and classifying, using the one or more processors, using the hyperspectral reflectance information and the Raman spectroscopy information, the subject as having one or more AD-associated pathologies, the one or more AD-associated pathologies including protein aggregates, the protein aggregates including at least one of Tau neurofibrillary tangles, Amyloid Beta deposits, soluble Amyloid Beta aggregates, or Amyloid precursor protein.

23. A computer program product by a machine learning training process, the computer program product comprising instructions stored in a non-transitory computer readable medium which, when executed by a computer, causes the computer to carry out non-invasive in vivo detection of one or more Alzheimer's Disease (AD)-associated pathologies from an eye of a subject, the machine learning training process comprising:

training, using one or more processors, the computer program using verified training data, the verified training data obtained by:

slicing an ex vivo tissue sample from a subject into tissue slices;

placing the tissue slices onto slides;

staining a first tissue slice of a first slide;

providing a second slide having a second tissue slice that was adjacent to the first tissue slice in the tissue sample and is unstained;

verifying that the stained first tissue slice has one or more of the AD-associated pathologies using histology;

performing at least one imaging modality on the second slide to obtain imaging information; and classifying the imaging information as being indicative of one or more of the AD-associated pathologies, the one or more AD-associated pathologies including protein aggregates, the protein aggregates including at least one of Tau neurofibrillary tangles, Amyloid Beta deposits, soluble Amyloid Beta aggregates, or Amyloid precursor protein.

24. The computer program product of claim 23, wherein the verified training data is further obtained by co-registering the first tissue slice with the second tissue slice.

25. The computer program product of claim 23, wherein the at least one imaging modality is a Raman spectroscopy unit, a hyperspectral reflectance imaging unit, or both the Raman spectroscopy unit and the hyperspectral reflectance imaging unit.

26. The computer program product of claim 23, wherein the performing at least one imaging modality comprises performing at least two imaging modalities which are collectively used for the classifying the imaging information as being indicative of one or more of the AD-associated pathologies.

27. A method for machine learning training of a computer program stored in a memory which, when executed by a computer, causes the computer to carry out non-invasive in vivo detection of one or more Alzheimer's Disease (AD)-associated pathologies from an eye of a subject, the method comprising:

training, using one or more processors, the computer program using verified training data, the verified training data obtained by:

slicing an ex vivo tissue sample from a subject into tissue slices;

placing the tissue slices onto slides;

staining a first tissue slice of a first slide;

providing a second slide having a second tissue slice that was adjacent to the first tissue slice in the tissue sample and is unstained;

verifying that the stained first tissue slice has one or more of the AD-associated pathologies using histology;

performing at least one imaging modality on the second slide to obtain detection information; and classifying the detection information as being indicative of one or more of the AD-associated pathologies, the one or more AD-associated pathologies including protein aggregates, the protein aggregates including at least one of Tau neurofibrillary tangles, Amyloid Beta deposits, soluble Amyloid Beta aggregates, or Amyloid precursor protein; and storing the trained computer program to the memory.

\* \* \* \* \*